US009075050B2

(12) United States Patent
Tsimikas et al.

(10) Patent No.: US 9,075,050 B2
(45) Date of Patent: Jul. 7, 2015

(54) METHODS FOR ASSESSING ATHEROGENESIS BY DETERMINING OXIDIZED PHOSPHOLIPID TO APOLIPOPROTEIN B RATIOS

(71) Applicant: The Regents of the University of California, Oakland, CA (US)

(72) Inventors: Sotirios Tsimikas, San Diego, CA (US); Joseph L. Witztum, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/048,809

(22) Filed: Oct. 8, 2013

(65) Prior Publication Data

US 2014/0309124 A1 Oct. 16, 2014

Related U.S. Application Data

(63) Continuation of application No. 13/400,392, filed on Feb. 20, 2012, now abandoned, which is a continuation of application No. 11/244,300, filed on Oct. 5, 2005, now Pat. No. 8,129,123.

(60) Provisional application No. 60/615,993, filed on Oct. 5, 2004.

(51) Int. Cl.
*G01N 33/53* (2006.01)
*G01N 33/92* (2006.01)

(52) U.S. Cl.
CPC ............. *G01N 33/5308* (2013.01); *G01N 33/92* (2013.01); *G01N 2333/775* (2013.01); *G01N 2800/32* (2013.01); *G01N 2800/323* (2013.01)

(58) Field of Classification Search
None
See application file for complete search history.

(56) References Cited

U.S. PATENT DOCUMENTS

| | | | |
|---|---|---|---|
| 5,364,612 | A | 11/1994 | Goldenberg |
| 6,375,925 | B1 | 4/2002 | Tsimikas et al. |
| 6,756,228 | B2 | 6/2004 | Tall et al. |
| 2003/0013688 | A1 | 1/2003 | Belder et al. |
| 2003/0109044 | A1 | 6/2003 | Logan et al. |
| 2007/0122419 | A1 | 5/2007 | Witztum et al. |
| 2010/0303769 | A1 | 12/2010 | Franco |
| 2011/0021419 | A1 | 1/2011 | Zimmer et al. |
| 2011/0059540 | A1 | 3/2011 | Hess et al. |

FOREIGN PATENT DOCUMENTS

| | | |
|---|---|---|
| EP | 0433088 A1 | 6/1991 |
| WO | 91/02252 A1 | 2/1991 |
| WO | 98/42751 A1 | 1/1998 |
| WO | 98/12561 A1 | 3/1998 |

OTHER PUBLICATIONS

Tsimikas et al., Temporal Increases in Plasma Markers of Oxidized Low-Density Lipoprotein Strongly Reflect the Presence of Acute Coronary Syndromes, Journal of the American College of Cardiology, vol. 41, No. 3, 2003 pp. 360-370.*
Wu et al., Autoantibodies to OxLDL are Decreased in Individuals with Borderline Hypertension, Hypertension, 1999; 33, pp. 53-59.*
Khoo et al., Monoclonal antibodies against LDL Further Enhance Macrophage Uptake of LDL Agregates, Arterioscler Thromb Vasc Biol. 1992; 12; pp. 1258-1266.*
Berglund et al., "Altered apoliporptein B metabolism in very low density lipoprotein from lovastatin-treated guinea pigs," Journal of Lipid Research, pp. 956-965, vol. 35, 1994.
Berglund et al., "Three-fold effect of lovastatin treatment on low density lipoprotein metabolism in subject with hyperlipidemia increase in receptor activity, decrease in apoB production, and decrease in particle affinity for the receptor: Results from a novel triple-tracer approach," J. of Lipid Research, 1998, pp. 913-924, vol. 39.
Chang et al., "Monoclonal antibodies against oxidized low-density lipoprotein bind to apoptotic cells and inhibit their phagocytosis by elicited macrophages: Evidence that oxidation-specific epitopes mediate macrophage recognition," Proc. Natl. Acad. Sci. USA, 1999, pp. 6353-6358, vol. 96, No. 11.
Frostegard et al., "Circulating oxidized low-density lipoprotein is increased in hypertension," Clinical Science, 2003, pp. 615-620, vol. 105.
Gillotte et al., "Oxidized phospholipids, linked to apolipoprotein B of oxidized LDL, are ligands for macrophage scavenger receptors," J. of Lipid Research, 2000, pp. 824-833, vol. 41.
Higuchi et al., "Human apolipoprotein B (apoB) mRNA: identification of two distinct apoB mRNAs an MRNA with the apoB-100 sequence and an apoB mRNA containing a premature in-frame translational stop codon, in both liver and intestine," Proc. Natl. Acad. Sci. USA, 1988, pp. 1772-1776, vol. 85.
Horkko et al., "Monoclonal autoantibodies specific for oxidized phospholipids or oxidized phospholipid-protein adducts inhibit macrophage uptake of oxidized low-density lipoproteins," J of Clin. Invest., 1999, pp. 117-128, vol. 103.
Itabe et al., "Sensitive detection of oxidatively modified low density lipoprotein using a monoclonal antibody," J. of Lipid Reserach, 1996, pp. 45-53, vol. 37.
Kiechl et al., "Oxidized Phospholipids, Lipoprotein(a), Lipoprotein-Associated Phospholipaase A2 Activity, and 10 year Cardiovascular Outcomes," Thromb. Vasc. Biol., 2007, pp. 1788-1795, vol. 27.

(Continued)

*Primary Examiner* — Gary W Counts
(74) *Attorney, Agent, or Firm* — Gavrilovich, Dodd & Lindsey LLP; Joseph R. Baker, Jr.

(57) ABSTRACT

The present invention provides methods to analyze oxidized phospholipids (OxPL) on apolipoprotein B-100 in patients at high risk or with documented coronary artery disease (CAD) or acute coronary syndromes (ACS) such as unstable angina and acute myocardial infarction or suspected of being at risk for ACS. Such methods are useful for diagnostic purposes and for monitoring the effects of dietary interventions or with drugs such as statins. More particularly, the disclosure provides methods for determining OxPL/apoB ratios as indices of atherosclerosis regression and plaque stability.

5 Claims, 8 Drawing Sheets

(56) References Cited

OTHER PUBLICATIONS

Lee et al., "All ApoB-Containing Lipoproteins Induce Monocyte Chemotaxis and Adhesion When Minimally Modified: Modulation of Lipoprotein Bioactivity by Platelet-Activating Factor Acetylhydrolase," Arterioscler. Thromb. Vasc. Biol., 1999, pp. 1437-1446, vol. 19.

Navab et al., "The oxidation hypothesis of atherogenesis," J. of Lipid Research, 2004, pp. 993-1007, vol. 45.

Palinski et al., "Low Density Lipoprotein Undergoes Oxidative Modification in vivo," Proc. Natl. Acad. Sci, USA, 1989, pp. 1372-1376, vol. 86.

Palinski et al., "Antisera and Monoclonal Antibodies Specific for Epitopes Generated during Oxidative Modification of Low Density Lipoprotein," Arteriosclerosis, 1990, pp. 325-335, vol. 10.

Palinski et al., "Cloning of Monoclonal Autoantibodies to Epitopes of Oxidized Lipoproteins from Apolipoprotein E-Deficient Mice," J. Clin. Invest. 1996, pp. 800-814, vol. 98.

Penny et al., "Improvement of Coronary Artery Endothelial Dysfunction with Lipid-Lowering Therapy: Heterogeneity of Segmental Response and Correlation with Plasma-Oxidized Low Density Lipoprotein," J. of the American College of Cardiology, 2001, pp. 766-774, vol. 37, No. 3.

Reardon et al., "Autoantibodies to OxLDL fail to alter the clearance of injected OxLDL in apolipoprotein E-deficient mice," J. of Lipid Research, 2004, pp. 1347-1354, vol. 45.

Schneider et al., "High-level lipoprotein (a) expression in transgenic mice: evidence of oxidized phospholipids in lipoprotein(a) but not in low density lipoproteins," 2004, pp. 769-778, vol. 46.

Tsimikas et al., "Oxidized Phospholipids, Lp(a) Lipoprotein, and Coronary Artery Disease," N. Engl. J. Med., 2005, pp. 46-57, vol. 353.

Tsimikas et al., "Increased Plasma Oxidation Phospholipid: Apolipoprotein B-100 Ratio With Concomitant Depletion of Oxidized Phospholipids from Atherosclerotic Lesions After Dietary Lipid-Lowering: A Potential Biomarker of Early Atherosclerosis Regression," Arterioscler. Thromb. Vasc. Biol., 2007, pp. 175-181, vol. 27.

Tsimikas et al., "Relationship of IgG and IgM autoantibodies to oxidized low density lipoprotein with coronary artery disease and cardiovascular events," J. of Lipid Research, 2007, pp. 425-433, vol. 48.

Tsimikas et al., "Percutaneous Coronary Intervention Results in Acute Increases in Oxidized Phospholipids and Lipoprotein(a): Short-term and Long-term Immunological Responses to Oxidized Low-Density Lipoprotein," Circulation, 2004, pp. 3164-3170, vol. 109.

Tsimikas et al., "High-Dose Atorvastatin Reduces Total Plasma Levels of Oxidized Phospholipids and Immune Complexes Present on Apolipoprotein B-100 in Patients with Acute Coronary Syndromes in the MIRACL Trial," Circulation, 2004, pp. 1405-1412, vol. 110.

Young, et al., "Two New Monoclonal Antibody-Based Enzyme-Linked Assays of Apolipoprotein B," Clin. Chem. 1986, pp. 1484-1490, vol. 32, No. 8.

Young et al., Characterization of an Abnormal Species of Apolipoprotein B, Apolipoprotein B-37, Associated with Familial Hypobetalipoproteinemia, J. of Clin. Invest., 1987, pp. 1831-1841, vol. 79.

\* cited by examiner

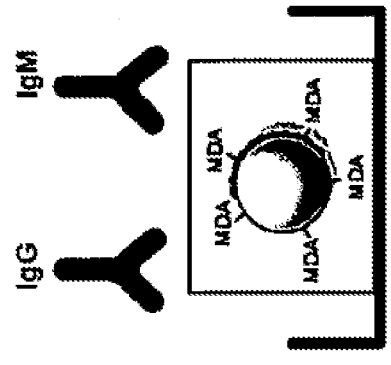
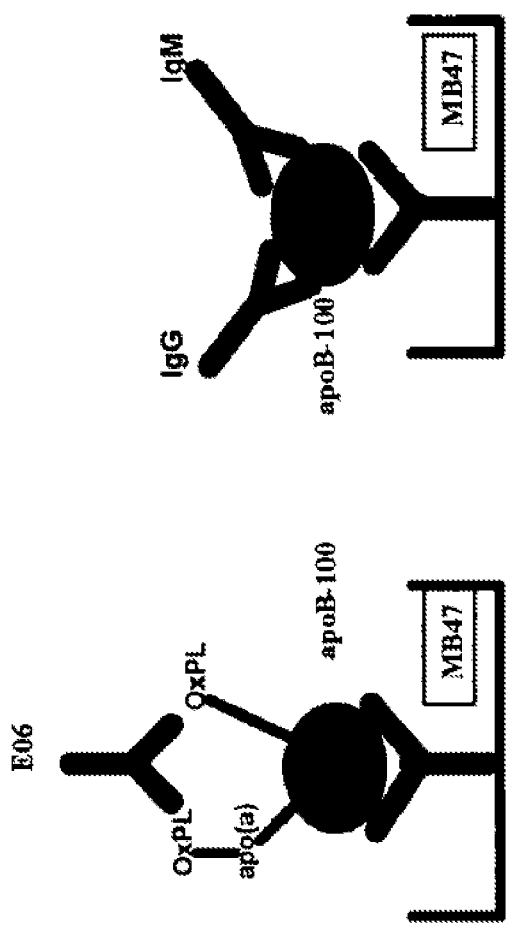

FIG. 4
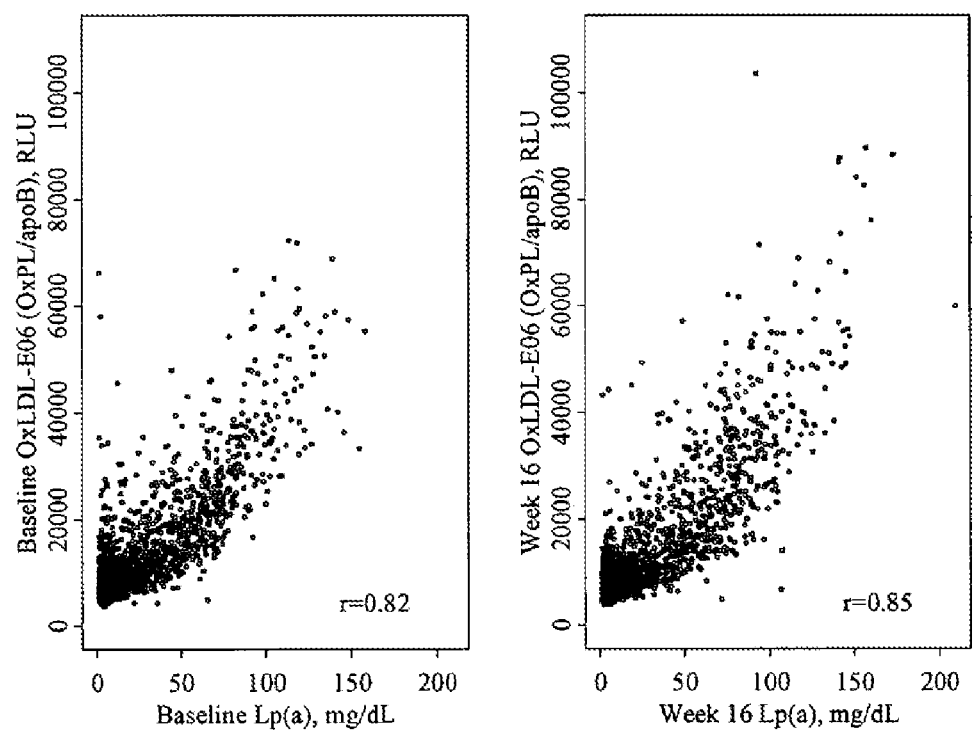
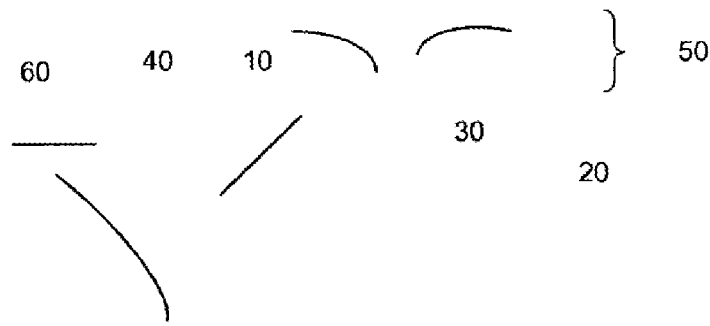

Frequency Distribution of the Oxidized Phospholipid:Apo B-100 Ratio (Panel A) and Lp(a) Lipoprotein Levels (Panel B).
Oxidized phospholipid:apo B-100 ratio denotes the oxidized phospholipid content per particle of apolipoprotein B-100.

METHODS FOR ASSESSING ATHEROGENESIS BY DETERMINING OXIDIZED PHOSPHOLIPID TO APOLIPOPROTEIN B RATIOS

CROSS REFERENCE TO RELATED APPLICATIONS

This application is a continuation of U.S. application Ser. No. 13/400,392, filed Feb. 20, 2012, which is a continuation of U.S. application Ser. No. 11/244,300, filed Oct. 5, 2005 (now U.S. Pat. No. 8,129,123), which claims priority from U.S. Provisional Application Ser. No. 60/615,993, filed Oct. 5, 2004, which is incorporated herein by reference.

STATEMENT REGARDING FEDERALLY SPONSORED RESEARCH

This invention was made with government support under grant number 56989 awarded by the National Heart, Lung, and Blood Institute (NHLBI). The government has certain rights in the invention.

TECHNICAL FIELD

The present invention relates to the analysis of oxidized phospholipids (OxPL) on apolipoprotein B-100 in patients at high risk or with documented coronary artery disease (CAD) or acute coronary syndromes (ACS) such as unstable angina and acute myocardial infarction or suspected of being at risk for ACS. Such methods are useful for diagnostic purposes and for monitoring the effects of dietary interventions or with drugs such as statins. More particularly, the present invention relates to methods for determining OxPL/apoB ratios as indices of atherosclerosis regression and plaque stability.

BACKGROUND

Atherosclerosis is a chronic inflammatory disease that results from hyperlipidemia and a complex interplay of a variety of environmental, metabolic and genetic risk factors. The oxidation of low density lipoprotein (OxLDL) plays a central, if not obligatory role, in the atherogenic process. Early studies showed that acetylation of LDL greatly enhanced its uptake by macrophages and that the uptake occurred via "scavenger receptors" which were distinct from the classical LDL receptor. Unlike most receptors, these scavenger receptors were not downregulated following uptake of OxLDL. Due to the excessive uptake of OxLDL and its associated lipid by the macrophages, the cells obtained a characteristic foam-like appearance. The appearance of such cells is one of the first hallmarks of atherosclerotic disease. Foam cells accumulate within the intima (under the endothelial lining) of the vessel walls where they lead to plaque formation, the hallmark of more advanced disease. Inflammatory conditions develop leading to the development of complicated lesions.

There is much evidence that OxLDL contributes to atherogenesis by a number of mechanisms. The oxidation of polyunsaturated fatty acids in phospholipids of lipoproteins generates many breakdown products such as malondialdehyde (MDA), 4-hydroxynonenal (4-HNE), and other reactive moieties attached to oxidized phospholipids. Many of these intermediate products are highly reactive and can interact with lysine residues of associated proteins and phospholipids to generate various adducts. These adducts are known to occur in vivo and are immunogenic. In murine models of atherosclerosis, such as apo-E deficient mice (ApoE$^{-/-}$) mice, atherosclerosis is correlated with the development of high titers of autoantibodies to various oxidation specific epitopes of OxLDL. The consequences of such cellular and humoral responses are still poorly understood, but under certain conditions they can clearly modify the natural history of the disease.

It is generally accepted that it is the composition of atherosclerotic lesions, in particular the content of lipids, OxLDL, foam cells, and smooth muscle cells that determines their properties. Foam cells are often found in the sites of lesion that are susceptible to rupture. Activated macrophages recruited to clear the apoptotic and necrotic foam cells, as well as OxLDL, secrete factors that weaken the plaque. Human pathology studies have shown that atheromas containing a large necrotic core, thin fibrous cap and large numbers of macrophage/foam cells in the shoulder are more predisposed to plaque rupture and thrombosis. These lesions, which frequently appear as mild or moderate coronary stenoses in angiographic studies, are characterized pathologically as large atheroma with extensive lipid pools exceeding 40% of plaque areas. Angiography only provides a measure of arterial lumen, but fails to detect vessel wall pathology. Diagnostic methods that provide a measure of the overall extent of the atherosclerotic lesion, with an emphasis on OxLDL and lipid content, would therefore be desirable. Moreover, the lipid core of atheromas can be assumed to contain extensive oxidized lipids that accumulated within foam cells and set free when cells undergo necrosis and apoptosis.

Non-invasive detection of atherosclerotic lesions can now be performed in animal models using imaging techniques that rely on antibodies that are specific for OxLDL. (See, for example, U.S. Pat. No. 6,716,410). Human studies have suggested that plaque rupture frequently occurs in non-angiographically significant lesions that contain abundant lipid-laden macrophages and large lipid pools within atheromas. Therefore imaging of atherosclerosis directed at lipid rich areas is of value, not only in detecting the extent of lesion burden, but also in the detecting clinically silent but "active" lesions.

In addition to such imaging techniques, there exists a need to develop simple noninvasive ways of studying atherogenesis that relate to the complexities of plaque biology rather than on plaque architecture or lipid profiles as a whole. Accordingly, the present invention relates to a plasma biomarker that specifically reflects plaque biology associated with atherogenesis.

SUMMARY

The present invention relates to methods for analyzing atherogenesis in a subject comprising the steps of determining the OxPL level in plasma, determining the apoB level in plasma, and then calculating the ratio of OxPL/apoB. This ratio provides a useful "atherogenesis index" (AI) for assessing patients at high risk or with documented coronary artery disease (CAD) or acute coronary syndromes (ACS) such as unstable angina and acute myocardial infarction or suspected of being at risk for ACS.

In one embodiment, a method of determining whether a therapy is effective for treating coronary artery disease, is provided. The method includes obtaining a first sample comprising plasma from a subject; administering a therapy to the subject; obtaining a second sample from the subject following administration of the therapy; determining the level of oxidized phospholipid (OxPL) in the first sample and second sample; determining the level of apoB in the first sample and the second sample; calculating an atherogenesis index (AI) by determining the ratio of the OxPL level to the apoB level for both samples. An increase in the ratio determined from the second sample in comparison to the ratio determined for the first sample, is indicative of an effective therapy for coronary artery disease. The information may be provided to a caregiver. In some embodiments, the therapy includes administering to the subject a composition comprising a compound that modulates the activity of HMG-CoA reductase, such as, for example, a statin.

In some embodiments, the level of OxPL and the level of apoB in the samples obtained from the subject are measured with two or more different biomolecules. The first biomolecule specifically interacts with OxPL and the second biomolecule specifically interacts with apoB. In some aspects, the biomolecules are antibodies, such as, for example, monoclonal antibodies. The antibody that interacts with OxPL may be, for example, E06 or DLH3.

In other aspects, the biomolecules are antigens. In some embodiments, the biomolecules are immobilized to form an array comprising a first set of a plurality of the first biomolecule and a second set of a plurality of the second biomolecule.

Exemplary oxidized phospholipid include oxidized forms of 1-palmitoyl-2-arachidonoyl-sn-glycero-3-phos-phorylcholine (Ox-PAPC), 1-palmitoyl-2-oxovaleroyl-sn-glycero-3-phosphoryl-choline (POVPC), 1-palrnitoyl-2-glutaroyl-sn-glycero-3-phosphorylcholine (PGPC), 1-palmitoyl-2-epoxyisoprostane-sn-glycero-3-phosphorylcholine (PEIPC), oxidized 1-stearoyl-2-arachidonoyl-sn-glycero-3-phosphorylcholin-e (Ox-SAPC), 1-stearoyl-2-oxovaleroyl-sn-glycero-3-phosphorylcholine (SOVPC, 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEIPE).

In another embodiment, the AI index is further correlated with, the age of the subject at the time the ratios are measured, the subject's gender, and/or the subject's race.

In another embodiment, an article of manufacture is provided. The article may include packaging material containing biomolecules that preferentially interact with oxidized phospholipid (OxPL) and apoB. The packaging material may include a label or package insert indicating that the biomolecules can be used for calculating an atherogenesis index (AI) by determining the ratio of the OxPL level to the apoB level.

In yet another embodiment, an array is provided. The array may include a substrate having a plurality of addresses, each address having disposed thereon a set of one or more biomolecules that specifically interact with oxidized phospholipid (OxPL) and apoB.

In another embodiment, a pre-packaged diagnostic kit for determining whether a therapy is effective for treating coronary artery disease, is provided. The kit may include an array as described above, instructions for using the array, and instructions calculating an atherogenesis index (AI) by determining the ratio of the OxPL level to the apoB level.

In other embodiments, a method for identifying plaque regression or stabilization in a blood vessel in a subject, is provided. The method includes obtaining a first sample comprising plasma from a subject; administering a therapy to the subject; obtaining a second sample from the subject following administration of the therapy; determining the level of oxidized phospholipid (OxPL) in the first sample and second sample; determining the level of apoB in the first sample and the second sample; calculating an atherogenesis index (AI) by determining the ratio of the OxPL level to the apoB level for both samples. An increase in the ratio determined from the second sample in comparison to the ration determined for the first sample, is indicative of an effective therapy for coronary artery disease. The information may be provided to a caregiver. In some embodiments, the therapy includes administering to the subject a composition comprising a compound that modulates the activity of HMG-CoA reductase, such as, for example, a statin.

In yet another embodiment, a method for determining the phospholipid content of an apoB-100 particle, is provided. The method includes obtaining a sample comprising apoB-100; determining the level of oxidized phospholipid (OxPL) in the sample; determining the level of apoB in the sample; and calculating an atherogenesis index (AI) by determining the ratio of the OxPL level to the apoB level.

As used herein, the terms "biological molecules" and "biomolecules" may be used interchangeably. These terms are meant to be interpreted broadly, and generally encompass polypeptides, peptides, oligosaccharides, polysaccharides, oligopeptides, proteins, oligonucleotides, and polynucleotides. Oligonucleotides and polynucleotides include, for example, DNA and RNA, e.g., in the form of aptamers. Biomolecules also include organic compounds, organometallic compounds, salts of organic and organometallic compounds, saccharides, amino acids, and nucleotides, lipids, carbohydrates, drugs, steroids, lectins, vitamins, minerals, metabolites, cofactors, and coenzymes. Biomolecules further include derivatives of the molecules described. For example, derivatives of biomolecules include lipid and glycosylation derivatives of oligopeptides, polypeptides, peptides, and proteins, such as antibodies. Further examples of derivatives of biomolecules include lipid derivatives of oligosaccharides and polysaccharides, e.g., lipopolysaccharides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other aspects of the invention are discussed throughout the specification.

DESCRIPTION OF THE DRAWINGS

FIG. 1A provides a schematic representation of the OxLDL assay for OxLDL-E06 (OxPL/apoB). The antibody E06 detects oxidized phospholipids (OxPL) present on apolipoprotein B-100 (apoB) and/or apolipoprotein (a) [apo(a)].

FIG. 1B provides a schematic representation of the OxLDL assay for apoB-Immune complexes (IC/apoB).

FIG. 1C provides a schematic representation of the OxLDL assay for autoantibodies to MDA-LDL.

FIG. 4 depicts the correlation between OxLDL-E06 (OxPL/apoB) and Lp(a) in all participants at baseline and 16 weeks.

FIG. 6, panel B, depicts the frequency distribution of the Lp(a) lipoprotein levels. Oxidized phospholipid:apo B-100 ratio denotes the oxidized phospholipid content per particle of apolipoprotein B-100.

DETAILED DESCRIPTION

Figure 2:
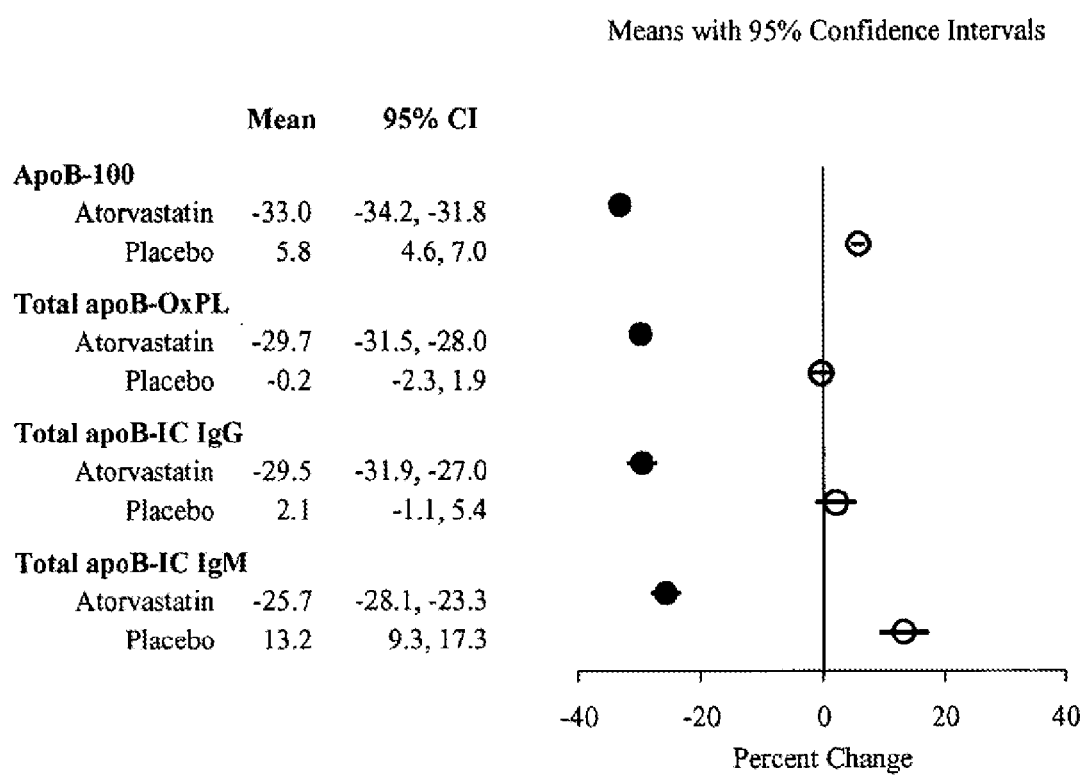
FIG. 2 depicts the geometric mean (95% CI) percent change from baseline to 16 weeks in apoB-100, total apoB-OxPL and total apoB-IC IgG and IgM in the atorvastatin and placebo groups.

The present invention relates to the analysis of OxPL of patients at high risk or with documented CAD or acute coronary syndromes (ACS) or suspected of being at risk for ACS. Such methods are useful for diagnostic purposes and for monitoring the effects of dietary interventions, as well as for monitoring treatment with anti-ACS drugs such as statins. More particularly, the present invention relates to methods for determining OxPL/apoB ratios as indices of atherosclerosis regression and plaque stability (i.e. "atherogenesis").

In one embodiment, a method of determining whether a therapy is effective for treating coronary artery disease, is provided. The method includes obtaining a first sample comprising plasma from a subject; administering a therapy to the subject; obtaining a second sample from the subject following administration of the therapy; determining the level of oxidized phospholipid (OxPL) in the first sample and second sample; determining the level of apoB in the first sample and the second sample; calculating an atherogenesis index (AI) by determining the ratio of the OxPL level to the apoB level for both samples. An increase in the ratio determined from the second sample in comparison to the ratio determined for the first sample, is indicative of an effective therapy for coronary artery disease. The information may be provided to a caregiver. In some embodiments, the therapy includes administering to the subject a composition comprising a compound that modulates the activity of HMG-CoA reductase, such as, for example, a statin.

In some embodiments, the level of OxPL and the level of apoB in the samples obtained from the subject are measured with two or more different biomolecules. The first biomolecule specifically interacts with OxPL and the second biomolecule specifically interacts with apoB. In some aspects, the biomolecules are antibodies, such as, for example, monoclonal antibodies. The antibody that interacts with OxPL may be, for example, E06 or DLH3.

In other aspects, the biomolecules are antigens. In some embodiments, the biomolecules are immobilized to form an array comprising a first set of a plurality of the first biomolecule and a second set of a plurality of the second biomolecule.

In one embodiment, the present invention relates to a method for measuring the plasma content of oxidized phospholipids on apolipoprotein B-100 particles (OxPL/apoB). For example, the content of OxPL and apoB may be measured with monoclonal antibodies that are specific for each of these OxPL constituents.

An exemplary biochemical test for identifying specific proteins, such as OxPL and apoB, employs a standardized test format, such as the Enzyme Linked Immunosorbent Assay or ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). It is understood that commercial assay enzyme-linked immunosorbant assay (ELISA) kits for various plasma constituents are available.

In another embodiment, the AI index is further correlated with, the age of the subject at the time the ratios are measured, the subject's gender, and/or the subject's race.

In another embodiment, an article of manufacture is provided. The article may include packaging material containing biomolecules that preferentially interact with oxidized phospholipid (OxPL) and apoB. The packaging material may include a label or package insert indicating that the biomolecules can be used for calculating an atherogenesis index (AI) by determining the ratio of the OxPL level to the apoB level.

In other embodiments, the invention provides methods for predicting the efficacy of a treatment for CAD through the use of proteomics. Proteomics is an evolving technology capable of testing for the presence of minute amounts of a vast array of proteins using small samples of human tissue. Using proteomic tools, increased or decreased levels of certain proteins in a biological sample such as serum can be ascertained. The invention encompasses plasma proteomic analysis as a non-invasive approach to determining whether a subject is responding to a treatment.

In yet another embodiment, an array is provided. The array may include a substrate having a plurality of addresses, each address having disposed thereon a set of one or more biomolecules that specifically interact with oxidized phospholipid (OxPL) and apoB.

The invention provides an array (i.e., "biochip" or "microarray") that includes immobilized biomolecules that facilitate the detection of a particular molecule or molecules in a biological sample. Biomolecules that identify the biomarkers described above can be included in a custom array for detecting OxPL or apoB. The array can also include biomolecules that identify additional factors indicative of the efficacy of a treatment for CAD. Additional biomolecules can be included in a custom array of the invention.

The term "array," as used herein, generally refers to a predetermined spatial arrangement of binding islands, biomolecules, or spatial arrangements of binding islands or biomolecules. Arrays according to the present invention that include biomolecules immobilized on a surface may also be referred to as "biomolecule arrays." Arrays according to the present invention that comprise surfaces activated, adapted, prepared, or modified to facilitate the binding of biomolecules to the surface may also be referred to as "binding arrays." Further, the term "array" may be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein may encompass biomolecule arrays, binding arrays, multiple arrays, and any combination thereof; the appropriate meaning will be apparent from context. The biological sample can include fluid or solid samples from any tissue of the body including plasma.

An array of the invention comprises a substrate. By "substrate" or "solid support" or other grammatical equivalents, herein is meant any material appropriate for the attachment of biomolecules and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TEFLON™, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins or agarose. Such coatings can facilitate the use of the array with a biological sample derived from serum.

A planar array of the invention will generally contain addressable locations (e.g., "pads", "addresses," or "microlocations") of biomolecules in an array format. The size of the array will depend on the composition and end use of the array. Arrays containing from about 2 different biomolecules to many thousands can be made. In some embodiments, the compositions of the invention may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates.

As an alternative to planar arrays, bead based assays in combination with flow cytometry have been developed to perform multiparametric immunoassays. In bead based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay.

Product formation of the biomarker with their immobilized capture biomolecules can be detected with a fluorescence based reporter system. Biomarkers can either be labeled directly by a fluorogen or detected by a second fluorescently labeled capture biomolecule. The signal intensities derived from captured biomarkers are measured in a flow cytometer. The flow cytometer first identifies each microsphere by its individual color code. Second the amount of captured biomarkers on each individual bead is measured by the second color fluorescence specific for the bound target. This allows multiplexed quantitation of multiple targets from a single sample within the same experiment. Sensitivity, reliability and accuracy are compared to standard microtiter ELISA procedures. With bead based immunoassay systems serum components can be simultaneously quantified from biological samples. An advantage of bead-based systems is the individual coupling of the capture biomolecule to distinct microspheres.

An array of the present invention encompasses any means for detecting a biomarker molecule such as, for example, apoB. For example, microarrays can be biochips that provide high-density immobilized arrays of recognition molecules (e.g., antibodies), where biomarker binding is monitored indirectly (e.g., via fluorescence). In addition, an array can be of a format that involves the capture of proteins by biochemical or intermolecular interaction, coupled with direct detection by mass spectrometry (MS).

Arrays and microarrays that can be used with the new methods to detect the biomarkers described herein can be made according to the methods described in U.S. Pat. Nos. 6,329,209; 6,365,418; 6,406,921; 6,475,808; and 6,475,809, and U.S. patent application Ser. No. 10/884,269, which are incorporated herein in their entirety. New arrays, to detect specific selections of sets of biomarkers described herein can also be made using the methods described in these patents.

Surfaces useful according to the present invention may be of any desired shape (form) and size. Non-limiting examples of surfaces include chips, continuous surfaces, curved surfaces, flexible surfaces, films, plates, sheets, tubes, and the like. Surfaces preferably have areas ranging from approximately a square micron to approximately 500 $cm^2$. The area, length, and width of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces and then placed into wells. In certain embodiments, such as where a surface without wells is used, binding islands may be formed or biomolecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

Modifications or binding of biomolecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," Drug Discovery Today 4(8):363-369 (1999), and references cited therein; Lakowicz J R, Principles of Fluorescence Spectroscopy, 2nd Edition, Plenum Press (1999).

In another embodiment, a pre-packaged diagnostic kit for determining whether a therapy is effective for treating coronary artery disease, is provided. The kit may include an array as described above, instructions for using the array, and instructions calculating an atherogenesis index (AI) by determining the ratio of the OxPL level to the apoB level.

Arrays of the invention suitable for identifying coronary artery disease, and the efficacy of a treatment therefore, may be included in kits. Such kits may also include, as non-limiting examples, reagents useful for preparing biomolecules for immobilization onto binding islands or areas of an array, reagents useful for detecting modifications to immobilized biomolecules, or reagents useful for detecting binding of biomolecules from solutions of interest to immobilized biomolecules, and instructions for use. Likewise, arrays comprising immobilized biomolecules may be included in kits. Such kits may also include, as non-limiting examples, reagents useful for detecting modifications to immobilized biomolecules or for detecting binding of biomolecules from solutions of interest to immobilized biomolecules.

In other embodiments, a method for identifying plaque regression or stabilization in a blood vessel in a subject, is provided. The method includes obtaining a first sample comprising plasma from a subject; administering a therapy to the subject; obtaining a second sample from the subject following administration of the therapy; determining the level of oxidized phospholipid (OxPL) in the first sample and second sample; determining the level of apoB in the first sample and the second sample; calculating an atherogenesis index (AI) by determining the ratio of the OxPL level to the apoB level for both samples. An increase in the ratio determined from the second sample in comparison to the ration determined for the first sample, is indicative of an effective therapy for coronary artery disease. The information may be provided to a caregiver. In some embodiments, the therapy includes administering to the subject a composition comprising a compound that modulates the activity of HMG-CoA reductase, such as, for example, a statin.

In yet another embodiment, a method for determining the phospholipid content of an apoB-100 particle, is provided. The method includes obtaining a sample comprising apoB-100; determining the level of oxidized phospholipid (OxPL) in the sample; determining the level of apoB in the sample; and calculating an atherogenesis index (AI) by determining the ratio of the OxPL level to the apoB level.

The invention provides compositions and methods for the identification of a subject that may or may not be responding to a treatment for CAD or ACS such that a theranostic approach can be taken to test such individuals to determine the effectiveness of a particular therapeutic intervention (pharmaceutical or non-pharmaceutical) and to alter the intervention to 1) reduce the risk of developing adverse outcomes and 2) enhance the effectiveness of the intervention. Thus, the methods and compositions of the invention also provide a means of optimizing the treatment of a subject having such a disorder. The invention provides a theranostic approach to treating such a disorder by integrating diagnostics and therapeutics to improve the real-time treatment of a subject having, for example, CAD and/or ACS. Practically, this means creating tests that can identify which patients are most suited to a particular therapy, and providing feedback on how well a drug is working to optimize treatment regimens. In the area of diseases associated with atherosclerosis, theranostics can flexibly monitor changes in important parameters over time. For example, theranostic multiparameter immunoassays specific for a series of diagnostically relevant molecules such as OxPL or apoB can be used to follow the progress of a subject undergoing treatment. The markers provided herein are particularly adaptable for use in diagnosis and treatment because they are available in easily obtained body fluids such as blood or serum.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

In other embodiments, the invention provides databases and computerized methods of analyzing and storing data associated with treatment regimens for athersclerosis related diseases. A database generated by the methods and analyses described herein can be included in, or associated with, a computer system for determining whether a treatment is successful. The database can include a plurality of digitally encoded "reference" (or "control") profiles. Each reference profile of the plurality can have a plurality of values, each value representing a level of, for example, OxPL or apoB detected in blood or serum of an individual having, or predisposed to having, an atherosclerosis related disorder. Alternatively, a reference profile can be derived from an individual who is normal. Both types of profiles can be included in the database for consecutive or simultaneous comparison to a subject profile. The computer system can include a server containing a computer-executable code for receiving a profile and identifying from the database a matching reference profile that is diagnostically relevant to the subject profile. The identified profile can be supplied to a caregiver for diagnosis or further analysis.

Using standard programs, electronic medical records (EMR) can be accumulated to provide a database that combines, for example, AI index data with additional information such as the age of a patient or any other parameter useful for predicting whether or not a subject will or is responding to a treatment. Patient information can be randomly assigned a numerical identifier to maintain anonymity with testing laboratories and for security purposes. All data can be stored on a network that provides access to multiple users from various geographic locations.

Thus, the various techniques, methods, and aspects of the invention described herein can be implemented in part or in whole using computer-based systems and methods. Additionally, computer-based systems and methods can be used to augment or enhance the functionality described herein, increase the speed at which the functions can be performed, and provide additional features and aspects as a part of, or in addition to, those of the invention described herein.

A processor-based system can include a main memory, preferably random access memory (RAM), and can also include a secondary memory. The secondary memory can include, for example, a hard disk drive and/or a removable storage drive, e.g., a floppy disk drive, a magnetic tape drive, or an optical disk drive. The removable storage drive reads from and/or writes to a removable storage medium. The removable storage medium can be a floppy disk, magnetic tape, optical disk, or the like, which is read by and written to by a removable storage drive. As will be appreciated, the removable storage medium can comprise computer software and/or data.

The computer system can also include a communications interface. Communications interfaces allow software and data to be transferred between the computer system and external devices. Examples of communications interfaces include a modem, a network interface (such as, for example, an Ethernet card), a communications port, a PCMCIA slot and card, and the like. Software and data transferred via a communications interface are in the form of signals, which can be electronic, electromagnetic, optical, or other signals capable of being received by a communications interface. These signals are provided to a communications interface via a channel capable of carrying signals and can be implemented using a wireless medium, wire or cable, fiber optics or other communications medium. Some examples of a channel include a phone line, a cellular phone link, an RF link, a network interface, and other communications channels. In this document, the terms "computer program medium" and "computer usable medium" are used to refer generally to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, enable the computer system to perform the features of the methods discussed herein. In particular, the computer programs, when executed, enable the processor to perform the features of the invention. Accordingly, such computer programs represent controllers of the computer system.

In an embodiment where the elements are implemented using software, the software may be stored in, or transmitted via, a computer program product and loaded into a computer system using a removable storage drive, hard drive, or communications interface. The control logic (software), when executed by the processor, causes the processor to perform the functions of the methods described herein.

In another embodiment, the computer-based methods can be accessed or implemented over the World Wide Web by providing access via a Web Page to the methods of the invention. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the invention to launch an application to, for example, perform an analysis according to the invention.

LDL Architecture

Early atherosclerotic lesions are characterized by the appearance of lipid-rich "foam cells", which are monocyte/macrophages that have taken up lipoproteins and are localized in the subendothelial space. It is not native LDL that is taken up by these cells, since native LDL cannot induce cholesterol accumulation. In contrast, these cells take up modified forms of LDL, and in particular oxidized LDL. Oxidized LDL (OxLDL) contains OxPL in two distinctly different forms: it is present in the lipid phase of the OxLDL, or it is covalently attached to apolipoprotein B-100 (apoB-100) during LDL oxidation.

OxLDL Metabolism

OxPL are present in the vessel wall and are pro-inflammatory and proatherogenic. During cholesterol lowering by diet or drugs, such as HMG-CoA-reductase inhibitors (statins), the plasma levels of OxPL/apoB actually increase compared to placebo. Animal experiments show that there is depletion of OxPL from the vessel wall into the circulation. This implies that a measurement of OxPL/apoB reflects both plaque regression and plaque stabilization.

This is documented in two studies described below. In studies with cynomolgous monkeys that were first placed on atherogenic diets ("Pre-regression") for six months and then subjected to regression diets ("regression"), there was a depletion of OxPL epitopes within atherosclerotic lesions by immunostaining with antibody E06, while at the same time, there was an increase in plasma OxPL/apoB levels (see FIG. 5). These experimental data support an interpretation that the increase in OxPL/apoB in plasma is a reflection of net efflux of OxPL from the vessel wall.

LDL: Individual Components

OxPL:

A monoclonal antibody, designated E06 has been reported that binds specifically to the phosphorylcholine head group of oxidized but not native phospholipids[13, 19]. Accordingly, this antibody can be used to determine the level of oxidized phospholipids in the OxLDL complex. This antibody can be adapted for use in any immunoassay. For example, chemiluminescent ELISA assays are described elsewhere herein.

Additional antibodies have been described in the literature that can also bind OxPL, such as DLH3 (Itabe et al., *J Lipid Res.* 1996; 37:45-53).

ApoB:

The total apoB-100 level in plasma can be determined using known immunoassay techniques.

Lp(a):

Lp(a) consists of a particle of low-density lipoprotein cholesterol (LDL-C) linked by a disulfide bond to a large hepatically derived glycoprotein, apolipoprotein(a), which is structurally similar to plasminogen. In theory, then, Lp(a) could promote cardiovascular disease in two ways: its apolipoprotein(a) moiety could promote thrombogenesis and its LDL-C moiety could promote atherogenesis. The apolipoprotein portion of Lp(a) competitively displaces plasminogen from binding sites on both fibrin and endothelial cells. Lp(a) is associated with increased levels of plasminogen activator-inhibitor (PAI-1) and decreased activity of tissue plasminogen activator (t-PA). These effects all promote thrombosis and inhibit fibrinolysis. Lp(a) can, like LDL-C alone, be oxidized, taken up by macrophages, and recovered from atherosclerotic plaque. Lp(a) appears to facilitate the oxidation of LDL-C, and can impair endothelial function.

LDL: Relative Component Levels

As discussed herein, "OxLDL-E06" or "OxPL/apoB" is a measure of the content of oxidized phospholipids (OxPL) per apoB-100 particle. Also as discussed herein, "apoB-IC", or "IC/apoB", refers to the total amount of apoB in circulating LDL immune complexes. Collectively, the OxPL/apoB and IC/ApoB measurements are used to specifically quantify the content of OxPL and IC, respectfully, on each captured apoB particle.

Alternatively, the Total apoB-OxPL and Total apoB-IC measurements reflect the OxPL and IC content on all apoB-100 containing particles in plasma, and are determined by multiplying the plasma "OxPL/apoB" and "IC/apoB" values by the plasma apoB-100 levels.

Accordingly, the present invention relates to the measurement of OxPL/apoB with or without simultaneous measurement of IC/apoB levels and/or total OxPL/apoB and total IC/apoB as indices of atherogenesis.

Statins

Statins inhibit the enzyme, HMG-CoA reductase that controls the rate of cholesterol production in the body. These drugs lower cholesterol by slowing down the production of cholesterol and by increasing the liver's ability to remove the LDL-cholesterol already in the blood. The large reductions in total and LDL-cholesterol produced by these drugs results in large reductions in heart attacks and heart disease deaths.

Examples of commercially available statins include, for example, Lipitor™ from Pfizer (atorvastatin), Zocor™ from Merck (simvastatin), Pravachol™ from Bristol-Myers Squibb (pravastatin), Lescol™ from Novartis (fluvastatin) and Mevacor™ from Merck (lovastatin). These statins are routinely administered using well-known clinical protocols.

Using the methods described herein, statin treatment can be readily monitored for efficacy.

Statin Studies

Randomized trials have clearly shown that hydroxymethylglutaryl (HMG-CoA) reductase inhibitors (statins) reduce all-cause mortality and cardiovascular events in patients with stable coronary artery disease (CAD) when given over 5 years. Retrospective and observational studies have also suggested that statins given to patients with acute coronary syndromes (ACS) improve event-free survival over one year. The MIRACL study demonstrated that in-hospital initiation of 80 mg atorvastatin reduced recurrent ischemic events over a 16 weeks period. The PROVE-IT study recently demonstrated superior outcomes in patients with ACS following two years' treatment with 80 mg atorvastatin versus 40 mg pravastatin, resulting in median LDL cholesterol levels of 62 and 95 mg/dl, respectively.

The mechanisms underlying the early benefits of statins are not well delineated, but have been loosely attributed to plaque stabilization. However, it is not established whether statins exert their benefits primarily through reduction of LDL-cholesterol alone and/or through additional pleiotropic effects, such as direct anti-inflammatory or anti-oxidant actions. Although statins have been shown to reduce in vitro measures of oxidative stress, their effects on plasma OxLDL levels in patients, particularly those with ACS, are not well known.

Increased levels of OxLDL in the vessel wall and circulation are present in patients with unstable or "vulnerable" plaques, in ACS and are associated with endothelial dysfunction. In mouse and rabbit aortic atherosclerotic lesions, OxLDL becomes depleted following regression diets, out of proportion to LDL depletion or other measures of plaque regression. These reductions in OxLDL are associated with increased collagen and smooth muscle cell content, increased eNOS production and reduced inflammatory markers, suggesting that removal of OxLDL from the vessel wall may serve as an early marker of plaque stabilization. In this analysis of the MIRACL trial, we determined whether favorable changes in plasma OxLDL levels may provide insights into the early clinical benefits of intensive statin treatment following ACS.

Example 1 a. Study Design and Patient Sample

The MIRACL study design was previously published.[5] Briefly, the study recruited 3086 patients with unstable angina or non-Q-wave acute myocardial infarction between 24-96 hours after hospital admission at 122 centers in 19 countries. Patients were randomly assigned to double-blind treatment with atorvastatin 80 mg/day or placebo for 16 weeks. The primary efficacy measure was the time to first occurrence of death, nonfatal acute myocardial infarction, cardiac arrest with resuscitation, or worsening angina with new objective evidence of ischemia and requiring emergency re-hospitalization. 2739 patients completed the entire 16 week follow-up period, of whom 2442 had baseline blood samples and 2341 had baseline and Week 16 blood samples available for analysis. Blood was collected in EDTA and stored at −70° C. until analysis. Patients were analyzed on an intention-to-treat basis.

b. Determination of OxLDL-E06, Apolipoprotein B-100 Immune Complexes and OxLDL (MDA-LDL) Autoantibody Titers Chemiluminescent ELISA was used to measure OxLDL markers (FIG. 1A-1C). All samples for a given assay were run in a single assay and internal controls consisting of high and low standard plasma samples were included to detect potential variations between microtitration plates. Each sample was assayed in triplicate and data are expressed as relative light units (RLU) in 100 milliseconds. The intra-assay coefficients of variation for all assays were 6-10%.

OxLDL-E06 is a measure of the content of oxidized phospholipids (OxPL) per apoB-100 particle using the murine monoclonal antibody E06, which specifically binds to the phosphorylcholine head group of oxidized but not native phospholipids. A 1:50 dilution of plasma in phosphate-buffered saline (PBS) is added to microtiter wells coated with the monoclonal antibody MB47 (5 µg/ml), which specifically binds apoB-100 particles. Under these conditions, a saturating amount of apoB-100 is added to each well and consequently an equal number of apoB-100 particles are captured in each well for all assays. The content of OxPL per apoB-100 is then determined with biotinylated E06. In a previous study we directly measured the amount of apoB-100 bound in each well by the degree of binding of a biotinylated anti-apoB-100 antibody, and compared the OxPL RLU values alone to the ratio of OxPL RLU/apoB-100 RLU and found a correlation of $r^2=0.99$ (n=1500 samples, data not shown). Therefore, we arbitrarily assigned the apoB-100 RLU value in the denominator as 1 and report the OxPL/apoB values as OxPL RLU counts only. Note that by design, this assay normalizes the OxPL content per apoB-100 particle and is therefore independent of plasma apoB-100 (and thus LDL-cholesterol) levels.

The data for OxLDL-E06 and apoB-IC are presented in two ways: 1) as OxPL/apoB and IC/apoB, which specifically quantifies the content of OxPL and IC, respectively, on each captured apoB-100 particle, and 2) as Total apoB-OxPL and Total apoB-IC, which reflects the OxPL and IC content on all apoB-100 containing particles in plasma, by multiplying the plasma "OxPL/apoB" and "IC/apoB" value by the plasma apoB-100 levels measured independently as noted below.

Plasma titers of IgG and IgM apoB-IC and malondialdehyde (MDA-LDL) (1:200 plasma dilution) autoantibodies and apoB-IC were measured, c. Lipoprotein (a) and ApoB-100 Levels Lp(a) is a modified LDL particle to which apo(a) is covalently linked. We have recently shown that a strong correlation exists between plasma OxLDL-E06 and Lp(a) levels and that 75-90% of the E06 immunoreactivity on apoB-100 particles is associated specifically with Lp(a) at steady state. E06 immunoreactivity is found in both the lipid and protein moieties of Lp(a), and kringle V of apolipoprotein (a) appears to contain up to 2 moles of covalently bound OxPL. However, in some settings, such as immediately following percutaneous coronary intervention (PCI), OxPL are found equally on apoB-100 particles without apo(a) and Lp(a).

Plasma Lp(a) levels were measured by a chemiluminescent ELISA with monoclonal antibody LPA4, as previously described. LPA4 does not cross-react with plasminogen. ApoB-100 levels were measured by a commercially available kit (Behring) and CRP levels as previously described.

d. Statistical Analysis

Since the baseline and Week 16 distributions of the OxLDL markers were positively skewed, log-transformed values were used in the statistical models and analyses and antilog-transformed for descriptive statistics yielding geometric means and 95% confidence intervals (CI) for baseline, Week 16 and percent change from baseline to Week 16. Inferential analyses included paired-sample t-tests for within treatment group differences in markers at baseline versus Week 16, and independent-sample t-tests for between treatment group differences in markers at Week 16 and between treatment group differences in absolute change in log-transformed markers from baseline to Week 16. Logistic regression models were constructed to summarize the relationships between baseline OxLDL values and the primary efficacy measure of the trial. For each marker, the logistic regression model included terms for log-transformed marker and randomized treatment assignment; odds ratios were expressed as the relative odds for each one unit increase in the log-transformed marker. Pearson correlations were calculated to summarize the relationship between OxPL/apoB and Lp(a) at baseline and at Week 16. Statistical significance was defined as $P<0.05$.

a. Patient Characteristics:

Baseline characteristics did not differ significantly between groups (as shown below in Table 1) or compared to the entire MIRACL population and there were no significant differences between patients with and without available blood samples for analysis.

TABLE 1

Baseline characteristics of the 2341 study subjects

| Characteristic | Placebo (n = 1190) | Atorvastatin (n = 1151) |
|---|---|---|
| Age, mean (SD), years | 64 (11) | 65 (11) |
| Men, n (%) | 796 (67) | 752 (65) |
| Presenting Syndrome, n (%) | | |
| Unstable angina | 534 (45) | 527 (46) |
| Non-Q wave myocardial infarct | 656 (55) | 624 (54) |
| Past myocardial infarct, n (%) | 288 (24) | 269 (23) |
| Prior coronary revascularization, n (%) | 131 (11) | 109 (9) |
| Hyperlipidemia, n (%) | 408 (34) | 421 (35) |
| Hypertension, n (%) | 636 (53) | 629 (55) |
| Diabetes mellitus type II, n (%) | 280 (24) | 251 (22) |
| Total cholesterol, mean (SD), mg/dl | 207 (37) | 206 (38) |
| LDL cholesterol, mean (SD), mg/dl | 125 (33) | 124 (34) |
| HDL cholesterol, mean (SD), mg/dl | 46 (12) | 47 (12) |
| Triglycerides, mean (SD), mg/dl | 186 (93) | 182 (86) |

For the 2442 patients with baseline data, 10.7% had an endpoint in the atorvastatin group and 12.8% in the placebo group during the 16-week follow-up period. Among the entire MIRACL population, 14.6% suffered a primary endpoint event in the atorvastatin group, compared with 17.2% in the placebo group. Thus, the incidence of recurrent events was lower in the present analysis cohort than the entire MIRACL population, but the risk reduction associated with atorvastatin treatment was similar.

b. Effect of Atorvastatin on OxLDL Markers and Lp(a):

Baseline levels of apoB-100, Total apoB-OxPL, Total apoB-IC, MDA-LDL autoantibodies and Lp(a) did not differ between groups. The atorvastatin-treated group had a 42% reduction in LDL cholesterol (124±34 to 72±35 mg/dL, P<0.0001) while the placebo-treated group had modest increases (124±34 to 135±37 mg/dL, P<0.0001). From baseline to Week 16, significant reductions in absolute and relative levels of apoB-100, Total apoB-OxPL, and Total apoB-IC (both IgG and IgM) were noted in the atorvastatin group compared to the placebo group: apoB-100, −33.0% vs. 5.8%; Total apoB-OxPL, −29.7% vs. −0.2%; Total apoB-IC IgG, −29.5% vs. 2.1% and Total apoB-IC IgM, −25.7% vs. 13.2%, P<0.0001 for all comparisons (see Table 2 below and FIG. 2).

TABLE 2

Baseline and 16 Week Mean Levels (95% confidence intervals) Of ApoB, OxLDL markers and Lp(a)

| Variable | Atorvastatin Baseline | Week 16 | P-Value** | Placebo Baseline | Week 16 | P-Value** | P-Value*** |
|---|---|---|---|---|---|---|---|
| ApoB-100* | 132 (130, 134) | 87 (85, 89) | <0.0001 | 133 (131, 135) | 138 (136, 140) | <0.0001 | <0.0001 |
| Total apoB-OxPL | 1297 (1252, 1342) | 912 (876, 949) | <0.0001 | 1300 (1257, 1344) | 1299 (1254, 1345) | 0.8290 | <0.0001 |
| Total apoB-IC IgG | 1067 (1030, 1106) | 749 (723, 778) | <0.0001 | 1090 (1051, 1131) | 1103 (1064, 1143) | 0.1963 | <0.0001 |
| Total apoB-IC IgM | 439 (421, 458) | 325 (311, 339) | <0.0001 | 456 (437, 477) | 517 (492, 542) | <0.0001 | <0.0001 |
| OxPL/apoB | 10085 (9770, 10409) | 11048 (10667, 11442) | <0.0001 | 10062 (9756, 10378) | 9690 (9356, 10036) | <0.0001 | <0.0001 |
| Lp(a)* | 11.9 (11.2, 12.6) | 13.0 (12.2, 14.0) | <0.0001 | 11.9 (11.2, 12.7) | 11.9 (11.1, 12.7) | 0.6164 | 0.0651 |
| IC/apoB | | | | | | | |
| IgG | 8323 (8069, 8585) | 9048 (8763, 9342) | <0.0001 | 8406 (8137, 8685) | 8204 (7944, 8472) | 0.2212 | <0.0001 |
| IgM | 3426 (3293, 3565) | 3933 (3785, 4087) | <0.0001 | 3525 (3387, 3669) | 3852 (3695, 4016) | <0.0001 | <0.0001 |
| Autoantibodies to MDA-LDL | | | | | | | |
| IgG | 4317 (4176, 4464) | 4922 (4772, 5076) | <0.0001 | 4587 (4451, 4728) | 5084 (4933, 5239) | <0.0001 | 0.1403 |
| IgM | 10025 (9696, 10365) | 1088 (10531, 11256) | <0.0001 | 10198 (9879, 10528) | 11256 (10895, 11627) | <0.0001 | 0.1608 |

For Total apoB-OxPL and Total apoB-IC IgG and IgM units are relative light units (RLU · mg/dl) × $10^3$
For OxPL/apoB, IgG and IgM IgG IC/apoB and autoantibodies to MDA-LDL units are in RLU
*units are mg/dl
**Within treatment group t-test p-values for changes Baseline to Week 16
***Atorvastatin vs. placebo t-test p-values for Week 16

In contrast, absolute OxPL/apoB levels increased significantly in the atorvastatin group, but actually decreased significantly in the placebo group (Table 2), suggesting that atorvastatin resulted in OxPL enrichment of apoB-100 particles, despite a reduction in Total apoB-OxPL levels. In parallel to the rise in OxPL/apoB, Lp(a) levels also increased to a similar extent in response to atorvastatin (Table 2). There was a significant relative increase in OxPL/apoB (9.5% vs. −3.9%) and Lp(a) levels (8.8% vs. −0.7%, P<0.0001 for both, FIG. 3) in the atorvastatin group compared to the placebo group. Indeed, strong correlations were noted between OxPL/apoB and Lp(a) at baseline (r=0.82) and Week 16 (r=0.85), P<0.0001 for both, FIG. 4. Similar correlations were noted for Total apoB-OxPL (data not shown). These findings are consistent with our previous observation that the OxPL recognized by E06 are predominantly associated with Lp(a).

Figure 3:
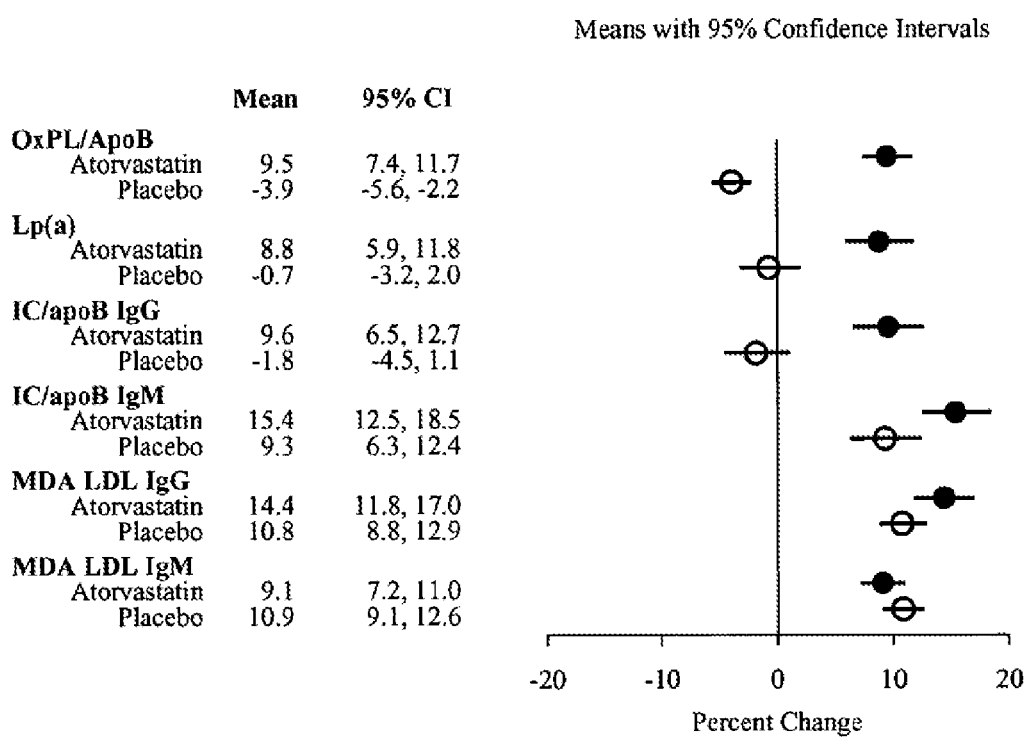
FIG. 3 depicts the geometric mean (95% CI) percent change from baseline to 16 weeks in OxLDL markers and Lp(a) in the atorvastatin and placebo groups.
Figure 5:
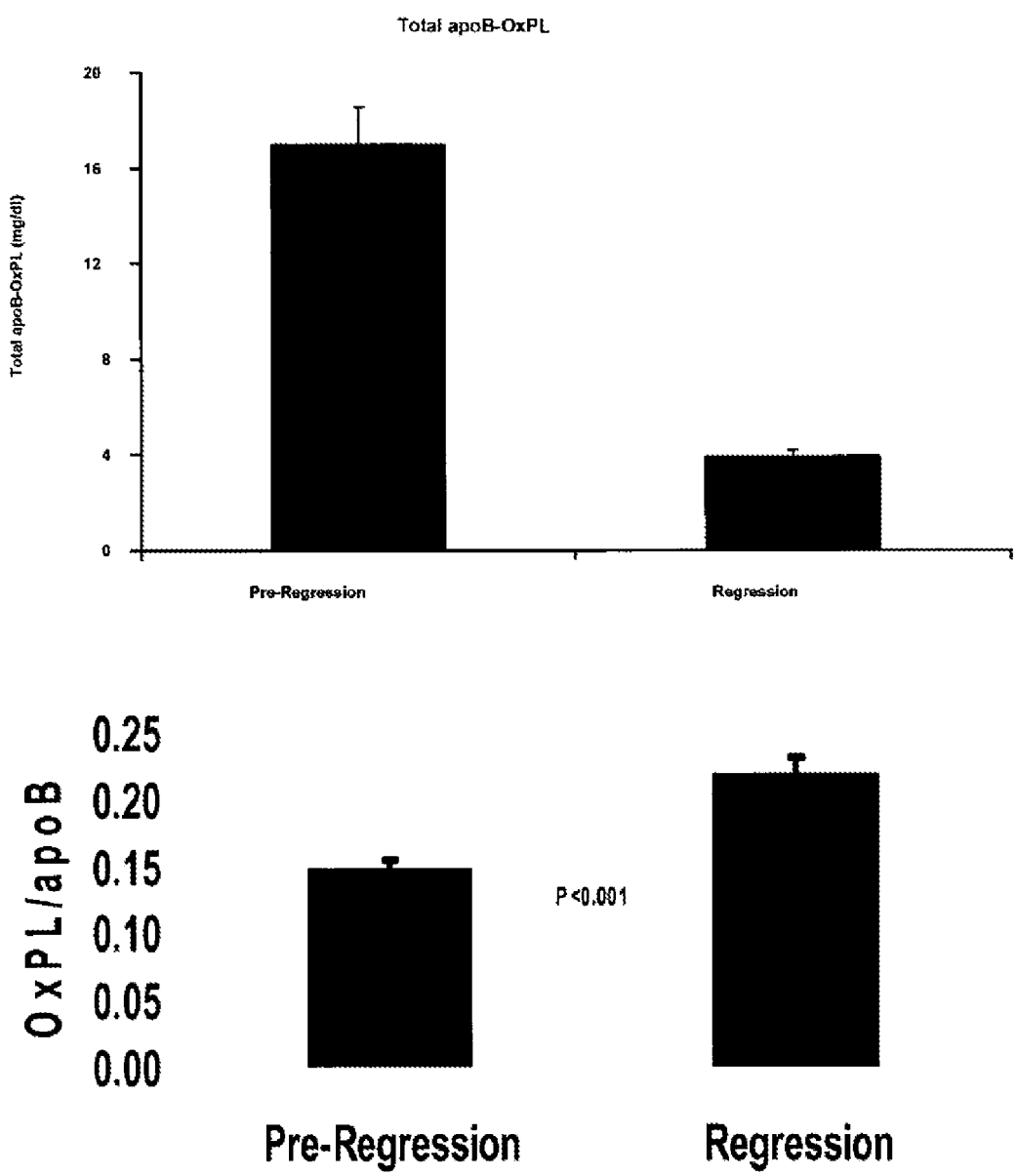
FIG. 5 depicts the change in total apoB-OxPL and OxPL/apoB ratio pre-regression and regression.

The relative increases in IgG IC/apoB (9.6% vs. −1.8%, P<0.0001) and IgM IC/apoB (15.4% vs. 9.3%, P=0.0053) were also higher in the atorvastatin group compared to placebo (FIG. 3). The IgG and IgM MDA-LDL autoantibody levels increased equally in both groups (range 9.1-14.4%, P<0.0001 for both, FIG. 3), as has been shown previously in ACS. The treatment group difference was significant for IgG (P=0.035) but not IgM (P=0.16). Pearson correlations between log-transformed CRP levels and OxLDL markers and Lp(a) at baseline and Week 16 were not statistically significant.

c. Relationship of Baseline OxLDL Markers and Lp(a) to Clinical Outcomes:

With increasing baseline levels of either Total apoB-IC IgM or IC/apoB IgM, there was reduced risk (odds ratio 0.81 for both) of recurrent events (P=0.032 and 0.013, respectively, FIG. 5). In this analysis, a one unit increase on the log scale was slightly greater than the interquartile range (the difference between the 25th and 75th percentiles). Baseline levels of other OxLDL markers, LDL-C, apoB-100 or Lp(a) were not predictive of risk at 16 weeks.

This study reveals that high-dose atorvastatin significantly reduced the total content of OxPL present on all circulating apoB-100 particles and suggests that the early clinical benefit of atorvastatin in ACS may be mediated in part through a reduction of vasoactive and pro-inflammatory OxPL in plasma. Interestingly, on average, individual apoB-100 particles at the new steady state were actually enriched in OxPL (i.e. an increased OxPL/apoB ratio), in conjunction with a strikingly similar increase in Lp(a), which we have previously shown binds OxPL. Although our observations do not establish a causal mechanism, we hypothesize that with the reduction of LDL cholesterol levels and inflammation, there ensues a mobilization of OxPL from the vessel wall, transient binding by apoB-100 particles [chiefly Lp(a)] and clearance from the circulation. In addition, these data provide further evidence for a novel physiological and/or pathophysiological role of Lp(a), which we and others have proposed binds and transports inflammatory OxPL.

It should be appreciated that different antibodies are used to detect oxidation epitopes on OxLDL and, depending on the epitope measured, different information may be obtained. We have therefore suggested that authors utilize the antibody used in their assay in their designation of OxLDL to call attention to this possibility at this early stage of such measurements. Thus, we designate our measure of OxLDL as OxLDL-E06 (OxPL/apoB). Because our assay was designed to provide a physical estimate of the OxPL epitope detected by E06 already normalized for apoB-100 levels, e.g. to yield OxPL/apoB, our methodology allows for two complementary but unique sets of measurements. First, it quantitates the number of E06 epitopes per apoB-100 particle [OxPL/apoB], which by design is independent of plasma LDL-cholesterol levels. Secondly, when the OxPL/apoB is multiplied by (independently measured) plasma apoB-100 levels, one derives Total apoB-OxPL levels present on all apoB-100 particles.

The role of statins in reducing plasma OxLDL in ACS has not been previously described. Based on the present study, it can be hypothesized that statin-mediated reduction in total plasma levels of OxPL and apoB-IC may be through both a reduction in the substrate for oxidation (i.e. reducing LDL levels and its associated lipids) and possibly through direct anti-inflammatory effects of atorvastatin metabolites, which have potent antioxidant effects. In vitro studies using several different statins, and/or their metabolites, demonstrate both a reduction in markers of generalized oxidative stress and LDL susceptibility to oxidation. For example, in patients with hypercholesterolemia, simvastatin has been shown to reduce the formation of $F_2$-isoprostanes and plasma OxLDL levels, although the epitope of OxLDL measured in this study was not defined. Moreover, statins also have other reported pleiotropic effects, at least in animal models, such as nitric-oxide sparing properties.

OxPL are known to be highly inflammatory and to induce vasoconstriction and it is possible that removal of such OxPL contributes to rapid improvement in endothelial function. This is supported by several studies showing improvement in coronary and brachial endothelial function with LDL apheresis or lovastatin treatment. More specifically, Tamai et al. have shown that acetylcholine-induced brachial artery vasodilatation rapidly improves within 4 hours following LDL apheresis [Lp(a) is also removed] and the best correlate of improvement was reduced plasma OxLDL levels, measured using monoclonal antibody DLH3, which binds to an OxPL epitope nearly identical to that bound by E06. Penny et al. have shown that OxPL-E06 was the best correlate of acetylcholine-induced coronary vasodilatation following lovastatin therapy in patients with CAD. LDL apheresis also decreases plasma concentrations of another model OxLDL, MDA-LDL, by 61%. A reduction in total OxPL may also produce anti-inflammatory effects which, in turn, may be related to clinical benefit of statin treatment. However, in this and previous studies, we have not found an association between any plasma OxLDL markers and CRP.

Our analyses also reveal the complementary observation that the plasma apoB particles of atorvastatin-treated patients were enriched in OxPL (an absolute 13.4% difference compared to placebo) despite the fact that there was an overall reduction in the content of total OxPL on all apoB-100 particles. What are the potential mechanisms of the increase in OxPL/apoB plasma levels following treatment with atorvastatin? In human studies, Crisby et al. have shown that 3-months' treatment with pravastatin prior to carotid endarterectomy markedly reduced OxLDL immunostaining in carotid plaques, using the oxidation-specific antibody NA59, which recognizes 4-hydroxynonenal oxidation-specific epitopes. Tsimikas et al. in an $LDLR^{-/-}$ mouse model and Aikawa et al. in a New Zealand White rabbit model, both using the oxidation-specific antibody MDA2, have shown decreased OxLDL content in aortic plaques following aggressive dietary lipid lowering. Additional unpublished data from both the murine and rabbit experiments, [which do not have Lp(a)], as well as similar studies with cynomolgus monkeys, show that following regression of established atherosclerosis by dietary induced lipid lowering, there are similar increases in OxPL/apoB plasma levels, but markedly diminished Total apoB-OxPL levels, similar to the MIRACL study. In all three animal studies, a direct immunochemical analysis of the arterial tissue with antibody E06 demonstrated a marked depletion of OxPL epitopes from the vessel wall, even as the plasma OxPL/apoB ratios were increased from the baseline measurements. Thus, in association with lesion regression, there was a clear net efflux of OxPL from the vessel wall at a time when the OxPL/apoB ratio in plasma was increased. (Tsimikas/Witztum, unpublished observations). In addition, unpublished in vitro data in our laboratory show that even in a PBS buffer there is preferential physical transfer of OxPL (derived from OxLDL) to Lp(a), compared to LDL. These data strongly support the hypothesis that the increase in OxPL/apoB associated with atorvastatin treatment is a surrogate marker of net OxPL efflux from the vessel wall. This hypothesis deserves further study.

Lp(a) levels were also modestly increased in response to atorvastatin in this study, which has previously been observed during the treatment of hypercholesterolemia with other statins, but has been underappreciated. One might speculate that increased Lp(a) levels occur in response to the enhanced efflux of OxPL from the vessel wall in order to facilitate their transport and elimination, though the mechanisms mediating such processes are unknown. In addition, it is also possible that anti-inflammatory and anti-atherogenic functions of HDL may have been improved by atorvastatin, leading to increased OxPL efflux. HDL, and in particular, a pre-beta fraction of HDL, may be the preferred initial acceptor of cholesterol from cellular sources. Recently, Navab et al. have observed that an apoA-I mimetic effects efflux of OxPL from cells to such a pre-beta HDL fraction and we speculate that in turn, Lp(a) would then preferentially accept such OxPL from the pre-beta HDL. This potential mechanism of efflux of OxPL from the vessel wall may be analogous to the rapid effects of ApoA-1/phospholipid complexes in reducing coronary atheroma volume, which presumptively also mobilized lipids out of the vessel wall. In support of this hypothesis is the recent observation that the OxPL/apoB ratio increased, as did Lp(a), in subjects consuming a low-fat diet, another condition in which one might speculate there was mobilization of OxPL from the artery wall.

In support of a potential transport function of OxPL by Lp(a), we have recently documented an ~50% increase in plasma OxLDL-E06 (i.e. OxPL/apoB) levels immediately following PCI, presumably released from disrupted plaques, with a simultaneous and similar increase in Lp(a) levels. Furthermore, the released OxPL epitopes were initially equally present on both apoB-100 and Lp(a) particles, but appeared to transfer to Lp(a) nearly exclusively by six hours. In patients presenting with ACS or undergoing PCI, we have also shown a strong association between plasma levels of OxLDL-E06 (OxPL/apoB) and Lp(a), further defining a novel pathophysiological association between OxPL and Lp(a).

It is also possible that Lp(a) directly contributes to the degradation of such OxPL, as Lp(a) was reported to be greatly enriched in platelet activating factor acetyl hydrolase, an enzyme that can degrade such OxPL. We have previously suggested that this potential physiological function of Lp(a) may be beneficial acutely, particularly in patients with normal Lp(a) levels. However, in patients with chronically elevated levels, Lp(a) with its predilection for enhanced binding to the extracellular matrix of atherosclerotic lesions, may be proinflammatory and proatherogenic because of the enhanced OxPL content.

The highest baseline levels of IgM IC/apoB and Total apoB-IC were associated with reduced risk of recurrent events (OR 0.81 and 0.84, respectively) and there was a similar trend with IgM MDA-LDL autoantibodies (OR 0.90). Although the underlying mechanisms are unclear, this suggests a potential protective effect of IgM OxLDL autoantibodies, as has been shown in animal models immunized with OxLDL or pneumococcal vaccine (which contains the same OxPL epitopes as OxLDL), which induce high circulating levels of OxLDL-specific IgM autoantibodies and decreased atherosclerosis. This is also consistent with previous studies showing an inverse correlation between IgM OxLDL autoantibody titers and CAD, hypertension, and carotid and femoral atherosclerosis.

Limitations of this study include the absence of blood samples at an intermediate timepoint during randomized treatment. Had samples been available for such measurements, the change in OxPL markers from baseline to the intermediate time point could have been related to the risk of an event following the intermediate time point. The high correlation of OxLDL-E06 with Lp(a) raises the question of whether measurements of OxLDL-E06 will provide incremental information above and beyond measurement of Lp(a). Additional experimental and appropriately powered clinical studies will be needed to establish whether OxPL markers are useful in predicting clinical outcomes. Nonetheless, our data do suggest novel physiological and/or pathophysiological functions of Lp(a) which warrant further investigation in future studies.

This study shows that atorvastatin therapy, compared to placebo, results in marked reduction in total plasma OxPL associated with apoB-100, while at the same time enlarging a pool of Lp(a) particles enriched in OxPL. These observations support the hypothesis that early atorvastatin treatment after ACS enhances mobilization and subsequent clearance of OxPL from the arterial wall, a mechanism that may contribute to the clinical benefit of statin therapy.

Example 2

Lp(a) lipoprotein binds proinflammatory oxidized phospholipids. We investigated whether levels of oxidized low-density lipoprotein (LDL) measured with use of monoclonal antibody E06 reflect the presence and extent of obstructive coronary artery disease, defined as a stenosis of more than 50 percent of the luminal diameter.

Levels of oxidized LDL and Lp(a) lipoprotein were measured in a total of 504 patients immediately before coronary angiography. Levels of oxidized LDL are reported as the oxidized phospholipid content per particle of apolipoprotein B-100 (oxidized phospholipid:apo B-100 ratio).

Measurements of the oxidized phospholipid:apo B-100 ratio and Lp(a) lipoprotein levels were skewed toward lower values, and the values for the oxidized phospholipid:apo B-100 ratio correlated strongly with those for Lp(a) lipoprotein (r=0.83, P<0.001). In the entire cohort, the oxidized phospholipid:apo B-100 ratio and Lp(a) lipoprotein levels showed a strong and graded association with the presence and extent of coronary artery disease (i.e., the number of vessels with a stenosis of more than 50 percent of the luminal diameter) (P<0.001). Among patients 60 years of age or younger, those in the highest quartiles for the oxidized phospholipid:apo B-100 ratio and Lp(a) lipoprotein levels had odds ratios for coronary artery disease of 3.12 (P<0.001) and 3.64 (P<0.001), respectively, as compared with patients in the lowest quartile. The combined effect of hypercholesterolemia and being in the highest quartiles of the oxidized phospholipid:apo B-100 ratio (odds ratio, 16.8; P<0.001) and Lp(a) lipoprotein levels (odds ratio, 14.2; P<0.001) significantly increased the probability of coronary artery disease among patients 60 years of age or younger. In the entire study group, the association of the oxidized phospholipid:apo B-100 ratio with obstructive coronary artery disease was independent of all clinical and lipid measures except one, Lp(a) lipoprotein. However, among patients 60 years of age or younger, the oxidized phospholipid:apo B-100 ratio remained an independent predictor of coronary artery disease.

Circulating levels of oxidized LDL are strongly associated with angiographically documented coronary artery disease, particularly in patients 60 years of age or younger. These data suggest that the atherogenicity of Lp(a) lipoprotein may be mediated in part by associated proinflammatory oxidized phospholipids.

Human coronary atherosclerosis is a chronic inflammatory disease that is superimposed on a background of lipid abnormalities. Proinflammatory oxidized low-density lipoprotein (LDL) may be a unifying link between lipid accumulation and inflammation in the vessel wall. In humans, oxidized LDL in plasma and within atherosclerotic lesions is strongly associated with coronary artery disease, acute coronary syndromes, and vulnerable plaques.

Lp(a) lipoprotein is a lipoprotein of unknown physiologic function that is composed of apolipoprotein B-100 (apo B-100) to which apolipoprotein(a) is covalently bound. Increased plasma levels of Lp(a) lipoprotein are independent predictors of the presence of angiographically documented and clinical coronary artery disease, particularly in patients with hypercholesterolemia. However, the underlying mechanisms by which Lp(a) lipoprotein contributes to the pathogenesis of atherosclerosis are not well understood. We recently showed that proinflammatory oxidized phospholipids are strongly associated with Lp(a) lipoprotein in human plasma. Therefore, we hypothesized that the presence of oxidized phospholipids on apo B-100-containing lipoproteins may explain some of the atherogenic properties of Lp(a) lipoprotein, and we designed this study to evaluate the relationship between circulating oxidized LDL, Lp(a) lipoprotein, and angiographically documented coronary artery disease.

We designed the current study on the basis of a previous study in which we had enrolled a total of 504 consecutive patients (97.2 percent of whom were white), 18 to 75 years of age, who were undergoing clinically indicated coronary angiography at the Mayo Clinic between June 1998 and December 1998.10 Race was self-reported. The exclusion criteria, which have been described previously, included prior coronary revascularization and the presence of diabetes mellitus. 10 Arterial plasma samples were obtained from the femoral sheath before angiography and were placed in tubes containing EDTA and frozen at 70° C. until the analyses were performed. Hypercholesterolemia was defined as a total cholesterol level of at least 250 mg per deciliter (6.5 mmol per liter), an LDL level of at least 150 mg per deciliter (3.9 mmol per liter), or ongoing treatment with lipid-lowering agents. The study was approved by the Mayo Clinic institutional review board, and all patients gave written informed consent. See Sotirios et al., "Oxidized Phospholipids, Lp(a) Lipoprotein, and Coronary Artery Disease," N Engl J Med 2005; 353:46-57, which is incorporated by herein by reference in its entirety.

The maximal stenosis in each of 27 coronary-artery segments was assessed by a cardiologist, who was unaware of risk factors, with the use of handheld calipers or in visual analysis according to the segmental classification system of the Coronary Artery Surgery Study. The extent of angiographically documented coronary artery disease was quantified as follows: normal coronary arteries (smooth, with either no stenosis or a stenosis of <10 percent of the luminal diameter), mild disease (a stenosis of 10 to 50 percent of the luminal diameter in one or more coronary arteries or their major branches), or onevessel, two-vessel, or three-vessel disease, defined as a stenosis of more than 50 percent of the luminal diameter in one, two, or three coronary arteries or their major branches.

Analyses of apo B-100, Lp(a) lipoprotein, total cholesterol, high-density lipoprotein (HDL) cholesterol, and triglycerides were performed with the use of commercially available kits. LDL cholesterol was estimated with the use of the Friedewald formula. High-sensitivity C-reactive protein (CRP) (lower limit of detection, 0.15 mg per liter) was measured as described elsewhere.

Our assay of oxidized LDL determines the content of oxidized phospholipids per particle of apo B-100 (oxidized phospholipid:apo B-100 ratio) and is performed with the use of the murine monoclonal antibody E06, which specifically binds to the phosphorylcholine moiety of oxidized but not native phospholipids. We have previously used the term OxLDL-E06 to describe the name of this assay. In brief, a dilution of plasma at 1:50 in phosphate-buffered saline was added to microtiter wells coated with monoclonal antibody MB47, which specifically binds apo B-100 particles. Under these conditions, a saturating amount of apo B-100 was added to each well, and consequently, equal numbers of apo B-100 particles were captured in each well for all assays. The oxidized phospholipid:apo B-100 ratio was measured by chemiluminescent enzyme-linked immunosorbent assay with the use of biotinylated E06, as described elsewhere.

Discrete data are presented as frequencies and percentages, and continuous variables as means and standard deviations or as medians and interquartile ranges if the distributions were skewed. Spearman's correlation coefficient was used to measure the linear associations between the rank values of the oxidized phospholipid:apo B-100 ratio and Lp(a) lipoprotein levels as well as lipid levels and other clinical risk factors. The association of the oxidized phospholipid:apo B-100 ratio and Lp(a) lipoprotein levels with the extent of coronary artery disease was tested by one-way analysis of variance of the log-transformed values followed by a one-degree-of-freedom test for trend. The percentages of patients with obstructive coronary artery disease and the odds ratios were calculated for quartiles of the oxidized phospholipid:apo B-100 ratio and Lp(a) lipoprotein levels for all patients, according to age (<60 years or >60 years), and according to the presenceor absence of hypercholesterolemia.

Logistic-regression models were used to estimate the associations between patients' characteristics and lipid measurements and obstructive coronary artery disease. Multiple logistic-regression analysis was used to estimate the partial associations between the oxidized phospholipid:apo B-100 ratio and Lp(a) lipoprotein levels and obstructive coronary artery disease, with adjustment for age, sex, smoking status, the presence or absence of hypertension, and levels of LDL cholesterol, HDL cholesterol, triglycerides, and CRP. The base-2 logarithms (log 2) of the oxidized phospholipid:apo B-100 ratio and the levels of Lp(a) lipoprotein, triglycerides, and CRP were used in all the logistic regression models to account for skewness in the distributions. Thus, odds ratios for these variables reflect the change in odds for an increase of 1 log 2 (the equivalent of a doubling of the value) in the measure.

Figure 6:
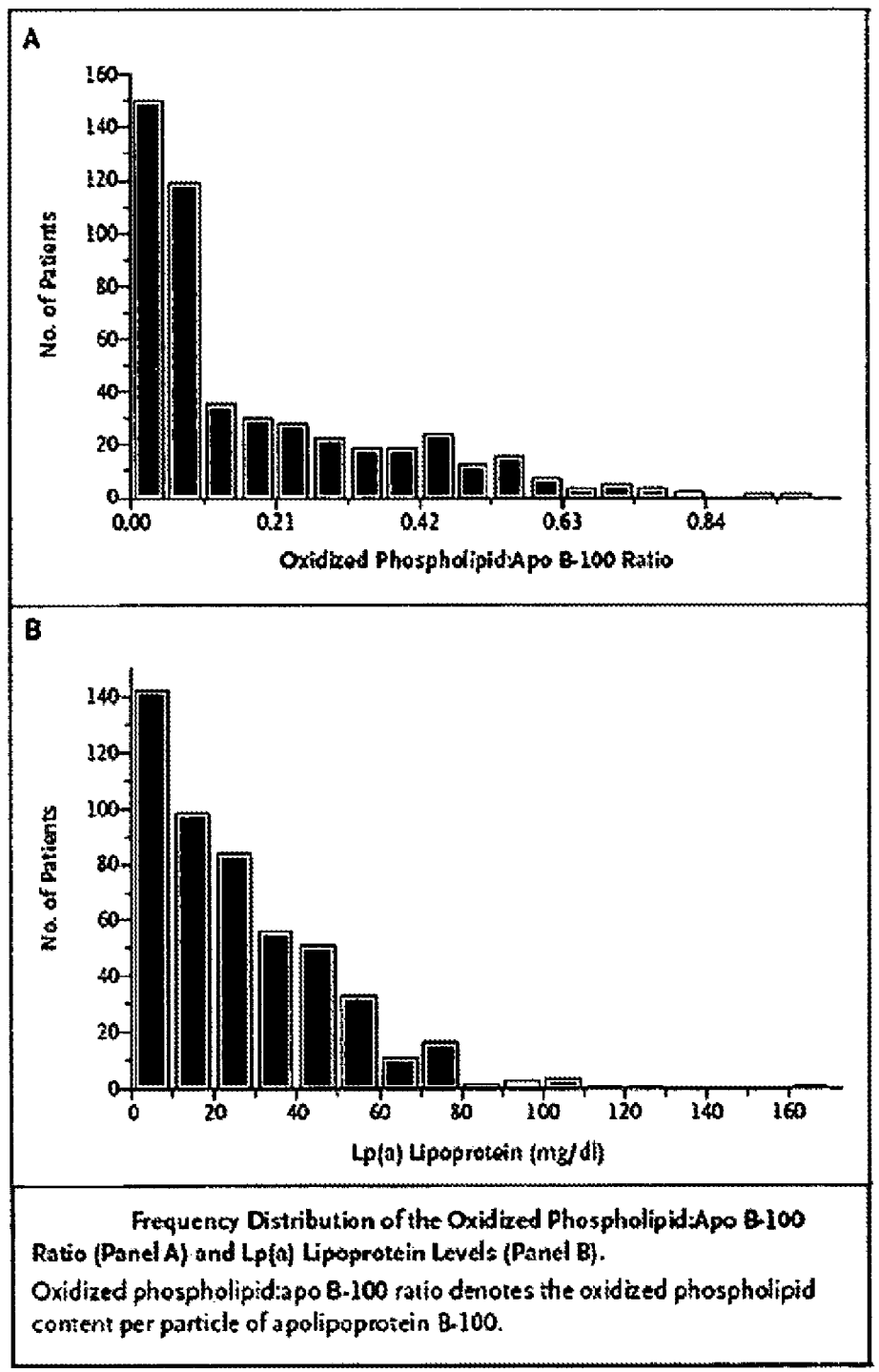
FIG. 6, panel A, depicts the frequency distribution of the oxidized phospholipid:Apo B-100 ratio.

The baseline clinical characteristics of the patients, indications for coronary angiography, lipid measurements, and CRP levels are shown in Table 3. The distributions of both the oxidized phospholipid:apo B-100 ratio and Lp(a) lipoprotein levels were skewed toward lower values, with 85 percent of the patients having levels lower than 0.4 and 45 mg per deciliter, respectively (FIG. 6). In the entire population, a strong correlation (r=0.83, P<0.001) was noted between the oxidized phospholipid:apo B-100 ratio and Lp(a) lipoprotein levels.

Figure 7:
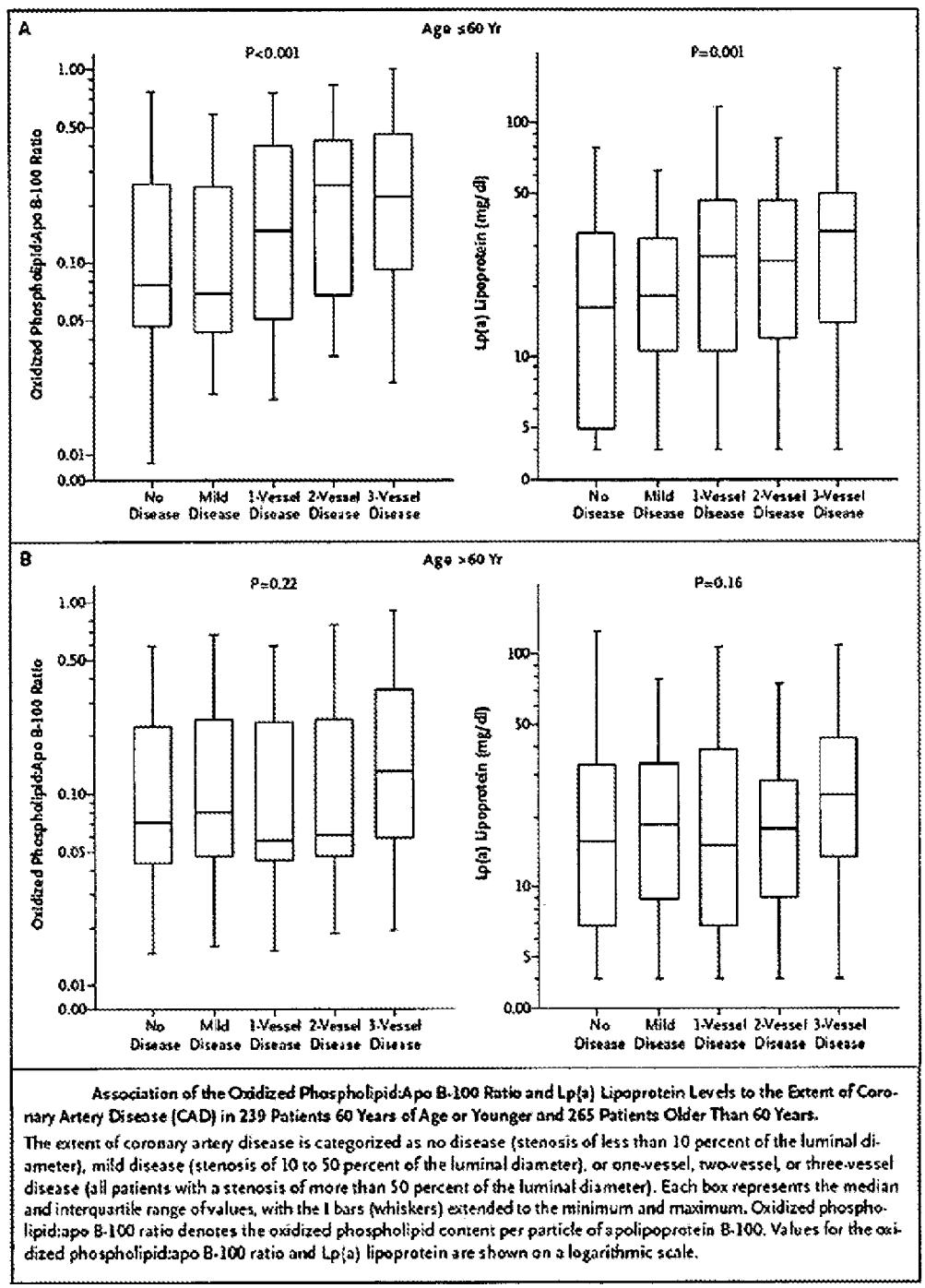
FIG. 7 depicts the association of the oxidized phospholipid:Apo B-100 ratio and Lp(a) lipoprotein levels to the extent of coronary artery disease (CAD) in 239 patients 60 Years of age or younger and 265 patients older than 60 years. The extent of coronary artery disease is categorized as no disease (stenosis of less than 10 percent of the luminal diameter), mild disease (stenosis of 10 to 50 percent of the luminal diameter), or one-vessel, two-vessel, or three-vessel disease (all patients with a stenosis of more than 50 percent of the luminal diameter). Each box represents the median and interquartile range of values, with the bars (whiskers) extended to the minimum and maximum. Oxidized phospholipid:apo B-100 ratio denotes the oxidized phospholipid content per particle of apolipoprotein B-100. Values for the oxidized phospholipid:apo B-100 ratio and Lp(a) lipoprotein are shown on a logarithmic scale.

Association with the Extent of Angiographically Documented Disease:

In the entire study group, the oxidized phospholipid:apo B-100 ratio and Lp(a) lipoprotein levels were strongly associated with a graded increase in the extent of coronary artery disease (P<0.001 for both analyses) (data not shown). These relationships were markedly stronger for patients 60 years of age or younger than for patients older than 60 years (FIG. 7).

Association with Obstructive Coronary Artery Disease:

The proportion of patients with obstructive coronary artery disease increased consistently with increases in the oxidized phospholipid:apo B-100 ratio and in Lp(a) lipoprotein levels (Table 4). This association was particularly evident among patients 60 years of age or younger, among whom the highest quartiles of the oxidized phospholipid:apoB-100 ratio (odds ratio, 3.12; P<0.001) and Lp(a) lipoprotein levels (odds ratio, 3.64, P<0.001) were associated with a significantly higher risk, as compared with the lowest quartiles. This association was not present among patients older than 60 years.

The combined effects of hypercholesterolemia plus either the oxidized phospholipid:apo B-100 ratio or Lp(a) lipoprotein levels greatly increased the probability of obstructive coronary artery disease. When compared with patients in the lowest quartile who did not have hypercholesterolemia, patients in the highest quartile of the oxidized phospholipid:apo B-100 ratio or Lp(a) lipoprotein levels who had hypercholesterolemia were significantly more likely to have obstructive coronary artery disease (Table 5). These relationships were markedly accentuated among patients 60 years of age or younger (for the oxidized phospholipid:apo B-100 ratio, odds ratio, 16.8 [P<0.001]; for Lp(a) lipoprotein levels, odds ratio, 14.2 [P<0.001]), as compared with those older than 60 years (for the oxidized phospholipid:apo B-100 ratio, odds ratio, 4.95 [P=0.003]; for Lp(a) lipoprotein levels, odds ratio, 4.92 [P=0.007]).

The relationship of the oxidized phospholipid:apo B-100 ratio and Lp(a) lipoprotein levels to coronary artery disease remained fundamentally similar after the exclusion from analysis of 41 patient with acute myocardial infarction within six weeks before enrollment. Also, there was a stronger association between the oxidized phospholipid:apo B-100 ratio and Lp(a) lipoprotein levels and coronary artery disease in patients with hypercholesterolemia who were taking statins than among such patients who were not taking statins, but differences in the odds ratios were not statistically significant.

Predictors of Obstructive Coronary Artery Disease:

Without adjustment for other risk factors, the oxidized phospholipid:apo B-100 ratio was predictive of obstructive coronary artery disease (odds ratio per doubling, 1.19; 95 percent confidence interval, 1.05 to 1.34; P=0.005) as was the Lp(a) lipoprotein level (odds ratio per doubling, 1.22; 95 percent confidence interval, 1.07 to 1.40; P=0.003). Similarly, male sex (odds ratio, 4.33; 95 percent confidence interval, 2.95 to 6.35; P<0.001), age (odds ratio per decade, 1.48; 95 percent confidence interval, 1.25 to 1.75; P<0.001), current smoking (odds ratio, 1.65; 95 percent confidence interval, 1.16 to 2.35; P=0.006), hypertension (odds ratio, 1.81; 95 percent confidence interval, 1.27 to 2.58; P=0.001), LDL cholesterol (odds ratio per increase of 25 mg per deciliter [0.65 mmol per liter], odds ratio, 1.28; 95 percent confidence interval, 1.12 to 1.45; P=0.003), and triglyceride levels (odds ratio per doubling, 1.27; 95 percent confidence interval, 1.00 to 1.61; P=0.05) were also predictive, whereas HDL cholesterol (odds ratio per increase of 10 mg per deciliter [2.3 mmol per liter], 0.64; 95 percent confidence interval, 0.56 to 0.74; P<0.001) was a negative predictor. CRP (odds ratio per doubling, 1.08; 95 percent confidence interval, 0.98 to 1.19; P=0.12) was not a predictor of obstructive coronary artery disease.

Among patients 60 years of age or younger, the odds ratios per doubling for the oxidized phospholipid:apo B-100 ratio (1.43; 95 percent confidence interval, 1.20 to 1.71; P<0.001) and Lp(a) lipoprotein level (1.41; 95 percent confidence interval, 1.16 to 1.73; P<0.001) were significant, whereas among those older than 60 years they were no longer significant (for the oxidized phospholipid:apo B-100 ratio:odds ratio per doubling, 1.05; 95 percent confidence interval, 0.89 to 1.25; P=0.58; and for Lp[a] lipoprotein levels:odds ratio per doubling, 1.09; 95 percent confidence interval, 0.90 to 1.32; P=0.37).

Multivariable analysis with the use of logistic regression models to derive adjusted odds ratios for coronary artery disease showed that an increase in the oxidized phospholipid: apo B-100 ratio (odds ratio per doubling, 1.21; 95 percent confidence interval, 1.05 to 1.39; P=0.007) was an independent predictor of obstructive coronary artery disease, as were male sex (odds ratio, 4.27; 95 percent confidence interval, 2.59 to 7.03; P<0.001), age (odds ratio per decade, 1.72; 95 percent confidence interval, 1.41 to 2.10; P<0.001), an increase in LDL cholesterol (odds ratio per 25 mg per deciliter, 1.28; 95 percent confidence interval, 1.11 to 1.48; P<0.001), and hypertension (odds ratio, 1.67; 95 percent confidence interval, 1.10 to 2.52; P=0.016), whereas an increase in HDL cholesterol levels (odds ratio per 10 mg per deciliter, 0.75; 95 percent confidence interval, 0.63 to 0.90; P=0.002) was a negative predictor. An increase in CRP (odds ratio per doubling, 1.09; 95 percent confidence interval, 0.97 to 1.22; P=0.16) was not a predictor of obstructive coronary artery disease. When Lp(a) lipoprotein was added to the model and the oxidized phospholipid:apo B-100 ratio was removed, Lp(a) lipoprotein was also an independent predictor (odds ratio per doubling, 1.20; 95 percent confidence interval, 1.02 to 1.40; P=0.02). As in the unadjusted data, the odds ratios per doubling for the oxidized phospholipid:apo B-100 ratio (1.49; 95 percent confidence interval, 1.20 to 1.84; P<0.001) and for Lp(a) lipoprotein (1.42; 95 percent confidence interval, 1.12 to 1.81; P=0.004) among patients 60 years of age or younger were significantly accentuated, whereas among those older than 60 years they were no longer significant (for the oxidized phospholipid:apo B-100 ratio:odds ratio per doubling, 1.00; 95 percent confidence interval, 0.82 to 1.22; P=0.96; for Lp(a) lipoprotein:odds ratio per doubling, 1.05; 95 percent confidence interval, 0.84 to 1.31; P=0.69).

Figure 8:
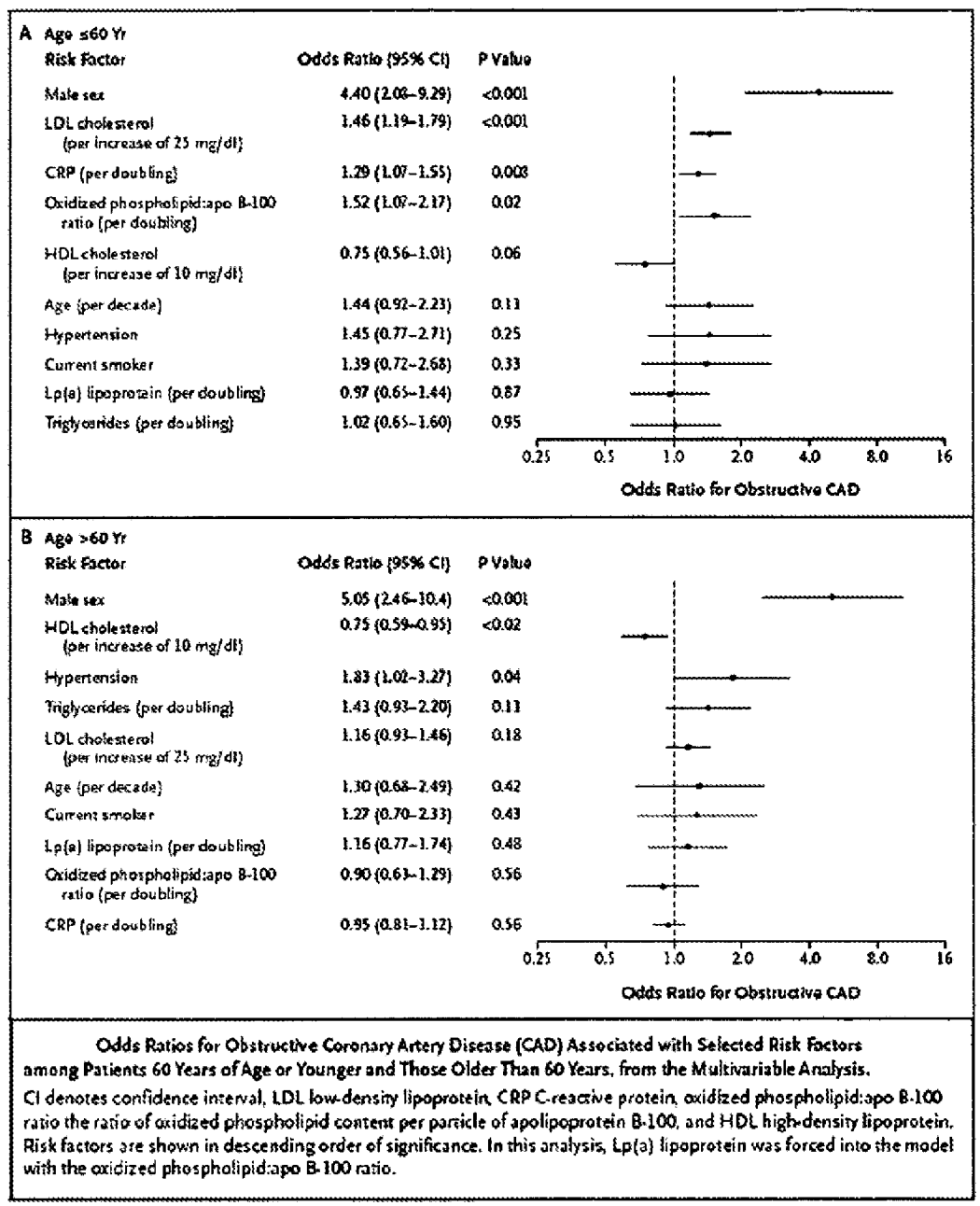
FIG. 8 depicts odds ratios for obstructive coronary artery disease (CAD) associated with selected risk factors among patients 60 years of age or younger and those older than 60 years, from the multivariable analysis. CI denotes confidence interval, LDL low-density lipoprotein, CRP C-reactive protein, oxidized phospholipid:apo B-100 ratio the ratio of oxidized phospholipid content per particle of apolipoprotein B-100, and HDL high-density lipoprotein. Risk factors are shown in descending order of significance. In this analysis, Lp(a) lipoprotein was forced into the model with the oxidized phospholipid:apo B-100 ratio.

Interestingly, in the entire study group, when Lp(a) lipoprotein was forced into the model with the oxidized phospholipid:apo B-100 ratio, there was a trend toward significance of the oxidized phospholipid:apo B-100 ratio (odds ratio per doubling, 1.21; 95 percent confidence interval, 0.95 to 1.54; P=0.12), whereas Lp(a) lipoprotein levels no longer remained an independent predictor of coronary artery disease (odds ratio per doubling, 1.00; 95 percent confidence interval, 0.76 to 1.32; P=0.99). However, when patients were analyzed according to age, the oxidized phospholipid:apo B-100 ratio, but not Lp(a) lipoprotein levels, was an independent predictor of obstructive coronary artery disease among those 60 years of age or younger, but not among those older than 60 years (FIG. 8). CRP was also a predictor of obstructive coronary artery disease among patients 60 years of age or younger, but not among those older than 60 years. When the 41 patients with acute myocardial infarction, who also had the highest levels of CRP, were removed from the analysis, CRP was no longer a predictor of obstructive coronary artery disease (odds ratio per doubling, 1.06; 95 percent confidence interval, 0.85 to 1.33; P=0.58), but the oxidized phospholipid:apo B-100 ratio (odds ratio per doubling, 1.55; 95 percent confidence interval, 1.05 to 2.27; P=0.03) remained a significant predictor. When the data were evaluated according to the absence of coronary artery disease, as compared with the presence of any coronary artery disease, the odds ratios were slightly smaller, but in general, the trends described were maintained, so that younger patients had higher odds ratios than older patients.

Correlations Between Oxidized LDL Levels and Other Biomarkers:

Levels of LDL cholesterol were weakly associated with levels of Lp(a) lipoprotein (r=0.17, P<0.001), and with the oxidized phospholipid:apo B-100 ratio (r=0.09, P=0.05). CRP levels correlated weakly with LDL cholesterol levels (r=0.10, P=0.02) and triglyceride levels (r=0.11, P=0.01). There were no significant correlations between the oxidized phospholipid:apo B-100 ratio or Lp(a) lipoprotein levels and CRP levels, age, body-mass index, blood pressure, and serum creatinine level.

This study shows an association between the oxidized phospholipid:apo B-100 ratio in plasma and the presence and extent of angiographically documented coronary artery disease. The association is independent of all clinical and lipid-related risk factors, except one, Lp(a) lipoprotein, which also has a strong association with angiographically documented coronary artery disease. The odds ratios for angiographically documented coronary artery disease associated with the Lp(a) lipoprotein level were nearly identical with those associated with the oxidized phospholipid:apo B-100 ratio. However, among patients younger than 60 years of age, the oxidized phospholipid:apo B-100 ratio remained an independent predictor of obstructive coronary artery disease. There was a strong correlation between levels of Lp(a) lipoprotein and the oxidized phospholipid:apo B-100 ratio. These observations, in conjunction with previous studies from our laboratory showing that in plasma such oxidized phospholipids are predominantly physically present on Lp(a) lipoprotein, 5-7,9 as opposed to other lipoproteins, lend strong support to the hypothesis that, in the setting of enhanced oxidative stress, proinflammatory.

Oxidized phospholipids may, in part, mediate the atherogenicity of Lp(a) lipoprotein. The natural murine monoclonal IgM autoantibody E06, cloned from apolipoprotein E receptor-deficient mice is functionally identical with classic natural T15 murine antibodies that bind phosphorylcholine on the cell-wall polysaccharide of pathogens such as pneumococcus and provide optimal protection from pneumococcal infections.13 In vitro, E06 binds to and prevents the uptake of oxidized LDL and apoptotic cells by scavenger receptors of macrophages. Binder et al. have also shown that the immunization of mice with *Streptococcus pneumoniae* results in increased titers of IgM oxidized LDL autoantibodies and reduction in the progression of atherosclerosis. These observations suggest that seemingly unrelated proatherogenic processes, such as oxidation, apoptosis, and infection, share molecular mimicry of the phosphorylcholine epitopes found on proinflammatory oxidized phospholipids.

Although previous studies have shown that plasma oxidized LDL levels are elevated in patients with clinically manifest stable coronary artery disease and acute coronary syndromes our study shows that oxidized phospholipids present on particles of apo B-100 and primarily on Lp(a) lipoprotein correlate with both the presence and extent of angiographically documented coronary artery disease. Although most of the oxidized LDL is present within the vessel wall, this study suggests that the small amounts of minimally modified LDL (e.g., particles of apo B-100 that contain oxidized phospholipids) are present in the circulation. This finding is also consistent with previous studies from our laboratory showing that the oxidized phospholipid:apo B-100 ratio (with oxidized LDL measured with use of antibody E06) rises abruptly after acute coronary events and immediately after percutaneous coronary intervention—situations in which the release of oxidized phospholipids (or oxidized LDL, or both) from the vessel wall might be postulated.

A potential pathophysiological relationship between levels of oxidized phospholipids and Lp(a) lipoprotein is strongly supported by this study and by data from earlier studies from our laboratory showing that oxidized phospholipids are physically associated with Lp(a) lipoprotein bound to lysine residues on isolated fragments of kringle V of apolipoprotein (a) 9 and also in the lipid phase of Lp(a) lipoprotein (unpublished data). In addition, the kringle V fragments containing such oxidized phospholipids induce inflammatory responses by up-regulating secretion of interleukin-8 by cultured human macrophages.

In this study, we have shown that the predictive abilities of levels of oxidized LDL and Lp(a) lipoprotein for obstructive coronary artery disease are highly interdependent. In the entire study group, when Lp(a) lipoprotein was excluded from the multivariable analysis, the odds ratios for the oxidized phospholipid:apo B-100 ratio were similar to those for traditional risk factors such as age, hypertension, and LDL cholesterol. Similarly, without the oxidized phospholipid:apo B-100 ratio in the analysis, Lp(a) lipoprotein levels stood as an independent predictor, as has been shown in a recent meta-analysis.8 In the entire study group, with the oxidized phospholipid:apo B-100 ratio in the model, there was no added ability of Lp(a) lipoprotein levels to explain the risk of obstructive coronary artery disease, suggesting that measures of oxidized LDL and Lp(a) lipoprotein represent a common path of biologic influence on the risk for coronary artery disease. However, in patients 60 years of age or younger, the oxidized phospholipid:apo B-100 ratio maintained its independent predictive power even with Lp(a) lipoprotein in the model. This observation supports the hypothesis that much of the risk attributable to Lp(a) lipoprotein levels can be explained by the binding of oxidized phospholipids by Lp(a) lipoprotein, but that in younger patients, an additional risk associated with oxidized phospholipids may be present, perhaps through proinflammatory pathways independent of Lp(a) lipoprotein.

The physiologic role of Lp(a) lipoprotein is unknown. We and others have suggested that a potential physiologic role of Lp(a) lipoprotein may be to bind and detoxify proinflammatory oxidized phospholipids. Lp(a) lipoprotein, which is present only in humans and Old World primates (although a partially related gene arose separately in hedgehogs), may have evolved to provide protection against various oxidative stressors. For example, Lp(a) lipoprotein has been shown to be involved in wound healing and possibly in preventing angiogenesis in tumor models, and elevated levels have been noted in centenarians in a manner consistent with human longevity.

Similarly, oxidized phospholipids are generated not only during atherogenesis but also in inflammation and apoptosis, which suggests that housekeeping functions involving the clearance of such oxidized phospholipids may have evolved for maintaining general health as well as vascular health. In this regard, Lp(a) lipoprotein may act in a way similar to CRP, which Chang et al. have shown also binds specifically to the phosphorylcholine moiety of oxidized phospholipids and apoptotic cells. Indeed, we and others have shown that Lp(a) lipoprotein acts as an acute-phase reactant in patients with acute coronary syndromes. It has also been reported to be highly enriched (higher by a factor of 7 than LDL) in platelet-activating factor acetyl hydrolase an enzyme that potentially could detoxify such oxidized phospholipids by removing the oxidized fatty acid.

Thus, when present at low levels, Lp(a) lipoprotein may serve a protective function by binding and participating in the transfer and possible degradation of oxidized phospholipids formed during normal homeostasis or in acutely stressful situations. However, when Lp(a) lipoprotein levels are chronically elevated (as determined genetically), especially in a milieu of chronically increased oxidative stress, Lp(a)\ lipoprotein, with its content of oxidized phospholipids, may be proatherogenic, particularly since it has enhanced binding to the extracellular matrix of the artery wall.

The association between the oxidized phospholipid:apo B-100 ratio and angiographically documented coronary artery disease in our study was much stronger for patients 60 years of age or younger than for older patients. The reasons for this association are not entirely clear, but many previous studies have documented a strikingly similar relationship between Lp(a) lipoprotein levels and angiographically documented disease among younger patients only. By excluding patients with diabetes and previous coronary revascularization from our study, we may have preferentially enriched the study group with younger patients with fewer traditional risk factors. In addition, increasing age, which is a surrogate for known and unknown risk factors, is itself one of the strongest risk factors for coronary artery disease. Thus, the independent effects of oxidized LDL and Lp(a) lipoprotein levels appear to diminish with age, presumably because of the cumulative contributions of additional risk factors that affect the clinical expression of atherosclerosis.

The limitations of this study include the fact that angiography is not a precise method for quantifying atherosclerosis. In addition, we have not yet defined the exact oxidized phospholipids, their physical location within Lp(a) lipoprotein, or the rates of flux, binding, and removal of oxidized phospholipids that are on Lp(a) lipoprotein. We have documented that plasma levels of oxidized phospholipids present on apo B-100-containing lipoproteins and predominantly on Lp(a) lipoprotein reflect the presence and extent of angiographically documented coronary artery disease. We propose that in settings of enhanced oxidative stress and elevated Lp(a) lipoprotein levels, a proinflammatory milieu may predominate that contributes to the clinical expression of cardiovascular disease.

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A kit comprising
a substrate that can be coated with an antibody;
a MB47 antibody that binds to apoB-100;
an IgG and an IgM antibody that bind to apoB-100;
an antibody that binds to oxidized phospholipid (OxPL).

2. The article of claim 1, wherein the MB47 antibody is coated on the substrate.

3. The article of claim 2, wherein the MB47 and antibody that binds to OxPL are monoclonal antibodies.

4. The article of claim 3, wherein the antibody that binds with OxPL is E06 or DLH3 and wherein the antibody is detectably labeled.

5. The article of claim 1, wherein the IgM and IgG antibody that binds to apoB-100 is detectably labeled.

* * * * *